US006852538B1

(12) United States Patent
Drouin et al.

(10) Patent No.: US 6,852,538 B1
(45) Date of Patent: Feb. 8, 2005

(54) NUR-RE A RESPONSE ELEMENT WHICH BINDS NUR NUCLEAR RECEPTORS AND METHOD OF USE THEREFOR

(75) Inventors: Jacques Drouin, Outremont (CA); Alexandra Philips, Sete (CA); Mario Maira, Montreal (CA)

(73) Assignee: Institut de Recherches Cliniques de Montreal, Montreal (CA)

( * ) Notice: Subject to any disclaimer, the term of this patent is extended or adjusted under 35 U.S.C. 154(b) by 0 days.

(21) Appl. No.: 09/319,782

(22) PCT Filed: Dec. 12, 1997

(86) PCT No.: PCT/CA97/00962

§ 371 (c)(1),
(2), (4) Date: Apr. 25, 2000

(87) PCT Pub. No.: WO98/26063

PCT Pub. Date: Jun. 18, 1998

(30) Foreign Application Priority Data

Dec. 12, 1996 (CA) .............................................. 3192754

(51) Int. Cl.$^7$ ........................ C12N 15/63; C12N 15/85; C12N 15/87; C07H 21/04
(52) U.S. Cl. ...................................... 435/455; 536/24.1
(58) Field of Search .......................... 536/24.1; 435/455

(56) References Cited

FOREIGN PATENT DOCUMENTS

| WO | WO 95/28482 | 10/1995 |
|---|---|---|
| WO | WO 96/21457 | 7/1996 |
| WO | WO 96/29405 | 9/1996 |
| WO | WO 96/41169 | 12/1996 |

OTHER PUBLICATIONS

N. Auphan, et al., "Immunosuppression by Glucocorticoids: Inhibition of NF–(kappa)B Activity through Induction of I(kappa)B Synthesis," Science 270:286–290, 1995.
E. Caldenhoven, et al., "Negative Cross–talk between ReIA and the Glucocorticoid Receptor: A Possibel Mechanism for the Antiinflammatory Action of Glucocorticoids," Mol. Endocrinol. 9(4):401–412, 1995.
L.E.–C. Cheng, et al., "Functional Redundancy of the Nur77 and Nor–1 Orphan Steroid Receptors In T–cell Apoptosis," EMBO J. 16(8): 1865–1875, 1997.
J. Drouin, et al., "Glucocorticoid Receptor Binding to a Specific DNA sequence is Required for Hormone–dependent Repression of Pro–opiomelanocortin Gene Transcription," Mol. Cell. Biol. 9(12):5305–5314, 1989.
J.H. Eberwine and J.L. Roberts, "Glucocorticoid Regulation of Pro–opiomelanocortin Gene Transcription in the Rat Pituitary," J. Biol. Chem. 259(4):2166–2170, 1984.
C. R. Egan, et al., "A Gut–to–pharynx/tall Switch In Embryonic Expression of the Caenorhabditis elegans ges–1 Gene Centers on Two GATA Sequences," Dev. Biol. 170:–397–419, 1995.

J.–P. Gagner and J. Drouin. "Opposite Regulation of Pro–opiomelanocortin Gene Transcription by Glucocarticoids and CRH," Mol. Cell. Endocrinol. 40:25–32, 1985.
J.–P. Gagner and J. Drouin, "Tissue–specific Regulation of Pituitary Proopiomelanocortin Gene Transcription by Corticotropin–releasing Hormone, 3', 5'–Cyclic Adenosine Monophosphate, and Glucocorticoids," Mol. Endocrinol. 1(10):677–682, 1987.
J. Godowski, et al., "Glucocorticoid Receptor Mutants that are Constitutive Activators of Transcriptional Enhancement," Nature 325:365–368, 1987.
S. Heck, et al., "A Distinct Modulating Domain in Glucocorticoid Receptor Monomers in the Repression of Activity of the Transcription Factor AP–1,"EMBO J. 13(17):4087–4095, 1994.
T. Heinzel, et al., "A Complex Containing N–CoR, mSin3 and Histone Deacetylase Mediates Transcriptional Repression," Nature 387:43–48, 1997.
A. Helmberg, et al., "Glucocorticoid–induced Apoptosis of Human Leukemic Cells is Caused by the Repressive Function of the Glucocorticoid Receptor," EMBO J. 14(3):452–460, 1995.
A. J. Horlein, et al., "Ligand–independent Repression by the Thyroid Hormone Receptor Mediated by a Nuclear Receptor Co–repressor," Nature 377:397–404, 1995.

(List continued on next page.)

Primary Examiner—James Ketter
Assistant Examiner—Konstantina Katcheves
(74) Attorney, Agent, or Firm—Quarles & Brady LLP

(57) ABSTRACT

The present invention relates to intracellular receptors, and methods for the modulation of transcription using same. More particularly, the invention relates to the Nur family of nuclear receptors. In general aspects, the present invention relates to the idenfication of a physiologically relevant response element (RE) for Nur family members, an ER–10 element as well as to the idenfication of the type of protein-protein interactions of Nur family member, enabling their specific interaction with this RE–10 and tfeir modulation of transcription at physiologically relevant sites. The invention further relates to methods for modulating processes mediated by such nuclear receptors. In addition, the invention relates to oligonucleotide sequences that bind regulatory proteins that affect transcription, such as the Nur family of nuclear receptors, to DNA constructs comprising the oligonucleotide sequences, cells transfected with the DNA constructs, to methods of using same to provide for the controlled expression of heterologous genes, and for the detection and recovery of new regulatory proteins. The present invention further provides bioassays for the identification of compounds as potential agonists or antagonists of transcription by the Nur family of nuclear receptors Moreover, the invention relates to the dissection of protein-rotein interactions or ligand-protein interactions involved in the modulation of transcription by the Nur family of nuclear receptors.

21 Claims, 19 Drawing Sheets

OTHER PUBLICATIONS

M. Iwata, et al., "Rescue of Thymocytes and T cell Hybridomas from Glucocorticoid–induced Apoptosis by Stimulation via the T cell Receptor/CD3 Complex: A Possible In Vitro Model for Positive Selection of the T cell Repertoire," Eur. J. Pharmacol. 21:643–648, 1991.

Y. Kamel, et al., "A CBP Integrator Complex Mediates Transcriptional Activation and AP–1 Inhibition by Nuclear Receptors," Cell 85:403–414, 1996.

T. K. Kerppola, et al., "Fox is a Preferential Target of Glucocortocoid Receptor Inhibition of AP–1 Activity In Vitro," Mol Cell. Biol. 13(6):3782–3719, 1993.

L.B. King, et al., "To Be or Not to Be: Mutually Antagonistic Death Signals Regulate Thymocyte Apoptosis," Int. Arch. All. Immunol. 105:355–358, 1994.

L.B. King, et al., "A Targeted Glucocorticoid Receptor Antisense Transgene Increases Thymocyte Apoptosis and Alters Thymocyte Development," Immunity 3:647–656, 1995.

H. Konig, et al., "Interference Between Pathway–specific Transcription Factors: Glucocorticoids Antagonize Phorbol Ester–induced AP–1 Activity without Altering AP–1 Site Occupation In Vivo," EMBO J. 11(6):2241–2246, 1992.

L. Nagy, et al., "Nuclear Receptor Repression Mediated by a Complex Containing SMRT, mSin3A, and Histone Deacetylase," Cell 89:373–380, 1997.

S. A. Onate, et al., "Sequence and Characterization of a Coactivator for the Steroid Hormone Receptor Superfamily," Science 270:1354–1357, 1995.

G. Poulin, et al., "NeuroD1/(beta)2 Contributes to Cell–specific Transcription of the Proopiomelanocortin Gene," Mol. Cell. Biol. 17(11):6673–6682, 1997.

R.I. Scheinman, et al., "Role of Transcriptional Activation of I(kappa)B(alpha) in Mediation of Immunosuppression by Glucocorticoids," Science 270:283–286, 1995.

R.I. Scheinman, et al., "Characterization of Mechanisms Involved in Transrepression of NF–(kappa)B by Activated Glucocorticoid Receptors," Mol. Cell. Biol. 15(2):943–953, 1995.

R. Sgonc, et al., "Simultaneous Determination of Cell Surface Antigens and Apoptosis," Trends Genet. 10:41–42, 1994.

Dominic J. Autelitano, et al., "Corticotrope responsiveness to glucocorticoids is modulated via rapid CRF–mediated induction of the proto–oncogene c–fos," Mole. Cell. Endocrin. 94:111–119, 1993.

Miguel Beato, "Gene Regulation by Steroid Hormones," Cell 56:335–344, 1989.

Miguel Beato, et al., "Steroid Hormone Receptors: Many Actors in Search of a Plot," Cell 83:851–857, 1995.

A. L. Boutillier, et al., "Corticotropin–Releasing Hormone Stimulates Proopiomelanocortin Transcription by cFos–Dependent and –Independent Pathways: Characterization of an AP1 Site in Exon 1," Mole. Endocrin. 9:745–755, 1995.

Barbara J. Calnan, et al., "A Role for the Orphan Steroid Receptor Nur77 in Apoptosis Accompanying Antigen–Induced Negative Selection," Immunity 3:273–282, 1995.

R. K. W. Chan, et al., "A Comparison of Two Immediate–Early Genes, c–fos and NGFI–B, as Markers for Functional Activation in Stress–related Neuroendocrine Circuitry," J. Neuroscience 13(12):5126–5138, 1993.

Ian Davis, et al., "Endocrine and Neurogenic Regulation of the Orphan Nuclear Receptors Nur77 and Nurr–1 in the Adrenal Glands," Mole. Cell. Biol. 14:3469–3483, 1994.

Jacques Drouin, et al., "Homodimer Formation Is Rate–Limiting for High Affinity DNA Binding by Glucocorticoid Receptor," Mole. Endocrin. 6:1299–1309, 1992.

Jacques Drouin, et al., "Novel glucocorticoid receptor complex with DNA element of the hormone–repressed POMC gene," EMBO J. 12:145–156, 1993.

Jacques Drouin, "Repression of transcription by nuclear receptors," Mech. Trans. Rep. pp. 118–140.

Jacques and Drouin, et al., "Selective Effect of Androgens on LH and FSH Release in Anterior Pituitary Cells in Culture," Endo. 98:1528–1534, 1976.

Jacques Drouin, et al., "Structure of the rat pro–opiomelanocortin (POMC) gene," Fed. Eur. Biol. Soc. 193:54–58, 1985.

Barry Marc Forman, et al., "Unique Response Pathways Are Established by Allosteric Interactions among Nuclear Hormone Receptors," Cell 81:541–550, 1995.

Vincent Giguèe, et al., "Determinants of Target Gene Specificity of RORα1: Monomeric DNA Binding by an Orphan Nuclear Receptor," Mole. Cell. Biol. 15:2517–2526, 1995.

Thomas G. Hazel, et al., "A gene inducible by serum growth factors encodes a member of the steroid and thyroid hormone receptor superfamily," Proc. Natl. Acad. Sci. USA 85:8444–8448, 1988.

Yoko Hirata, et al., "The Phosphorylation and DNA Binding of the DNA–binding Domain of the Orphan Nuclear Receptor NGFI–B*," J. Bio. Chem. 268:24808–24812, 1993.

Jari Honkaniemi, et al., "Induction of multiple immediate early genes in rat hypothalamic paraventricular nucleus after stress," Mole. Brain Res. 25:234–241, 1994.

Lauren Jacobson, et al., "Regulation of Proopiomelanocortin Gene Transcription," Pit. Gland 2:117–138, 1994.

Carsten Jonat, et al., "Antitumor Promotion and Antiinflammation: Down–Modulation of AP–1 (Fos/Jun) Activity by Glucocorticoid Hormone," Cell 62:1189–1204, 1990.

Thomas Lamonerie, et al., "Ptxl, a bicoid–related homeo box transcription factor involved in transcription of the pro–opiomelanocortin gene," Genes & Dev. 10:1284–1295, 1996.

Simon W. Law, et al., "Identification of a New Brain–Specific Transcription Factor, NURR1," Mole. Endocrin. 6:2129–2135, 1992.

Zheng–Gang Liu, et al., "Apoptotic signals delivered through the T–cell receptor of a T–cell hybrid require the immediate–early gene nur77," Nature 367:281–284, 1994.

Mar Maira, et al., "Heterodimerization between Members of the Nur Subfamily of Orphan Nuclear Receptors as a Novel Mechanism for Gene Activation," Mole. Cell. Biol. 19:7549–7557, 1999.

David J. Mangelsdorf, et al., "The Nuclear Receptor Superfaimly: The Second Decade," Cell 83:835–839, 1995.

David J. Mangelsdorf, et al., "The RXR Heterodimers and Orphan Receptors," Cell 83:841–850, 1995.

Jeffrey Milbrandt, "Nerve Growth Factor Induces a Gene Homologous to the Glucocorticoid Receptor Gene," Neuron 1:183–188, 1988.

Evelyn P. Murphy, et al., "Neuroendocrine Regulation of the Hypothalamic Pituitary Adrenal Axis by the nurr1/nur77 Subfamily of Nuclear Receptors," Mole. Endocrin. 16:39–47, 1997.

Akira Nakai, et al., "A Human Early Response Gene Homologous to Murine nur77 and Rat NGFI–B, and Related to the Nuclear Receptor Superfamily," *Mole. Endocrin.* 4:1438–1443, 1990.

Edward Oates, et al., "5' Sequence of Porcine and Rat Pro–opiomelanocortin mRNA," *J. Biol. Chem.* pp. 7421–7425, 1984.

Naganari Ohkura, et al., "Molecular Cloning of a Novel Thyroid/Steroid Receptor Superfamily Gene From Cultured Rat Neuronal Cells+," *Biochem. Biophys. Res. Comm.* 205:1959–1965, 1994.

David Parkes, et al., "Corticotropin–Releasing Factor Activates c–fos, NGFI–B, and Corticotropin–Releasing Factor Gene Expression within the Paraventricular Nucleus of the Rat Hypothalamus," *Mole. Endocrin.* 7:1357–1367, 1993.

Ragnhild E. Paulsen, et al., "Three Related Brain Nuclear Receptors, NGFI–B, Nurr1, and NOR–1, as Transcriptional Activators," *J. Mole. Neuro.* 6:249–255, 1995.

Thomas Perlmann, et al., "A novel pathway for vitamin A signaling mediated by RXR heterodimerization with NGFI–B and NURR1," *Genes & Dev.* 9:769–782, 1995.

Alexandre Philips, et al., "Antagonism between Nur77 and Gucocorticoid Receptor for Control of Transcription," *Mole. Cell. Biol.* 17:5952–5959, 1997.

Alexandre Philips, et al., "Novel Dimeric Nur77 Signaling Mechanism in Endocrine and Lymphoid Cells," *Mole. Cell. Biol.* 17:5946–5951, 1997.

Anna Tate Riegel, et al., "Proopiomelanocortin Gene Promoter Elements Required for Constitutive and Glucocorticoid–Repressed Transcription," *Mole. Endocrin.* 5:1973–1982, 1991.

Rolf–Peter Ryseck, et al., "Structure, mapping and expression of a growth factor inducible gene encoding a putative nuclear hormonal binding receptor," *EMBO J.* 8:3327–3335, 1989.

Magdalena Schräder, et al., "Thyroid Hormone Receptor Functions as Monomeric Ligand–induced Transcription Factor on Octameric Half–sites," *J. Biol. Chem.* 269:6444–6449, 1994.

Rol Schüle, et al., "Functional Antagonism between Oncoprotein c–Jun and the Glucocorticoid Receptor," *Cell* 62:1217–1226, 1990.

Marc Therrien, et al., "Pituitary Pro–Opiomelanocortin Gene Expression Requires Synergistic Interactions of Several Regulatory Elements," *Mole. Cell. Biol.* 11:3492–3503, 1991.

Marc Therrien, et al., "Cell–Specific Helix–Loop–Helix Factor Required for Pituitary Expression of the Pro–Opiomelanocortin Gene," *Mole. Cell. Biol.* 13:2342–2353, 1993.

Thomas E. Wilson, et al., "The Orphan Receptors NGFI–B and Steroidogenic Factor 1 Establish Monomer Binding as a Third Paradigm of Nuclear Receptor–DNA Interaction," *Mole. Cell. Biol.* 13:5794–5804, 1993.

Thomas E. Wilson, et al., "Identification of the DNA Binding Site for NGFI–B by Genetic Selection in Yeast," *Science* 252: 1296–1300, 1991.

Thomas E. Wilson, et al., "Participation of Non–Zinc Finger Residues in DNA Binding by Two Nuclear Orphan Receptors," *Science* 256:107–110, 1992.

Alan P. Wolfe, "Sinful Repression," *Nature* 387:16–17, 1997.

John D. Woronicz, et al., "Regulation of the Nur77 Orphan Steroid Receptor in Activation–Induced Apoptosis," *Mole. Cell. Biol.* 15:6364–6376, 1995.

John D. Woronicz, et al., "Requirement for the orphan steroid receptor Nur77 in apoptosis of T–cell hybridomas," *Nature* 367:277–281, 1994.

Hsin–Fang Yang–Yen, et al., "Transcriptional Interference between c–Jun and the Glucocorticoid Receptor: Mutual Inhibition of DNA Binding Due to Direct Protein–Protein Interaction," *Cell* 62:1205–1215, 1990.

Karina Yazdanbakhsh, et al., "Cyclosporin A blocks apoptosis by inhibiting the DNA binding activity of the transcription factor Nur77," *Proc. Natl. Acad. Sci. USA* 92:437–441, 1995.

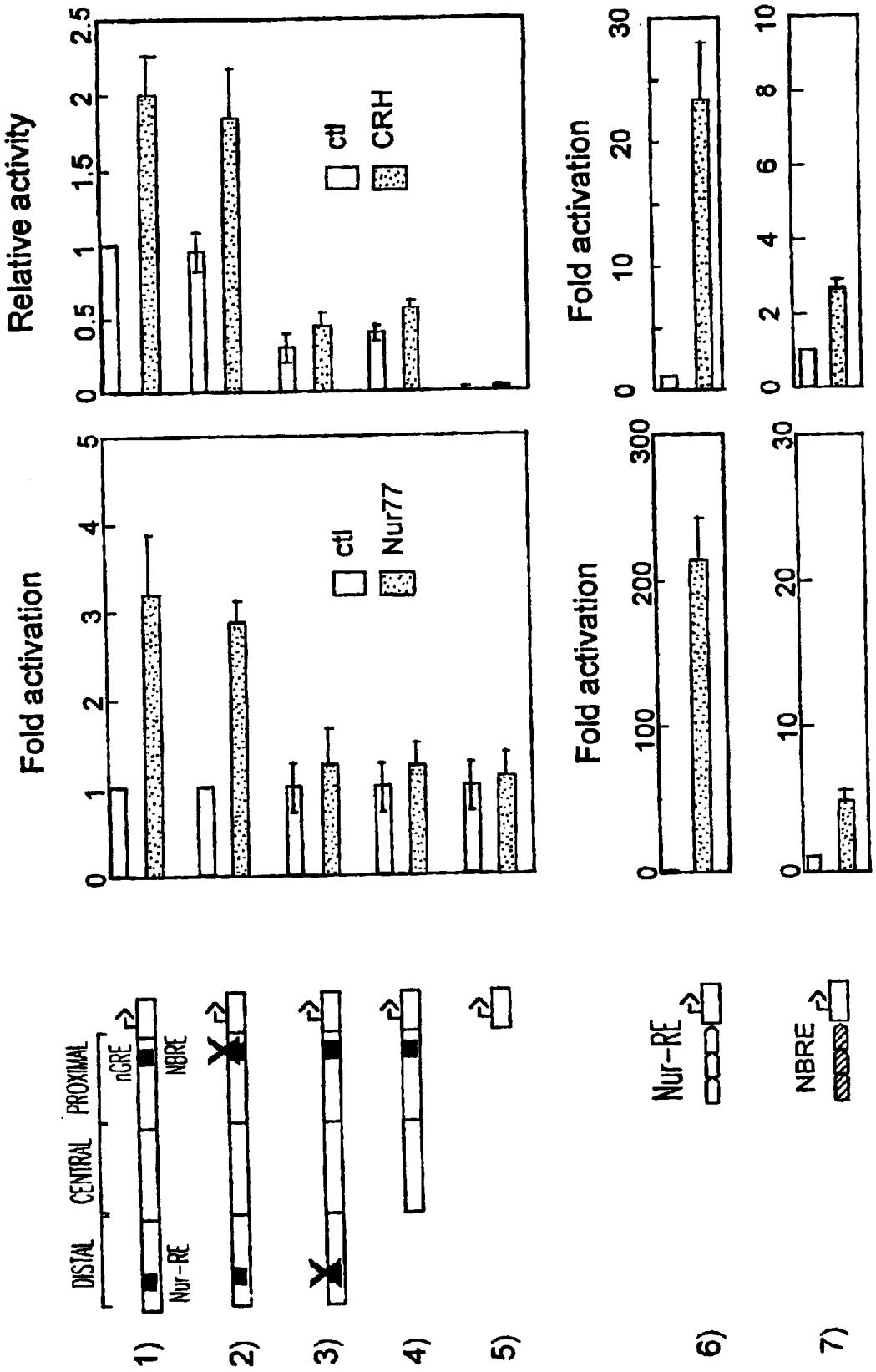

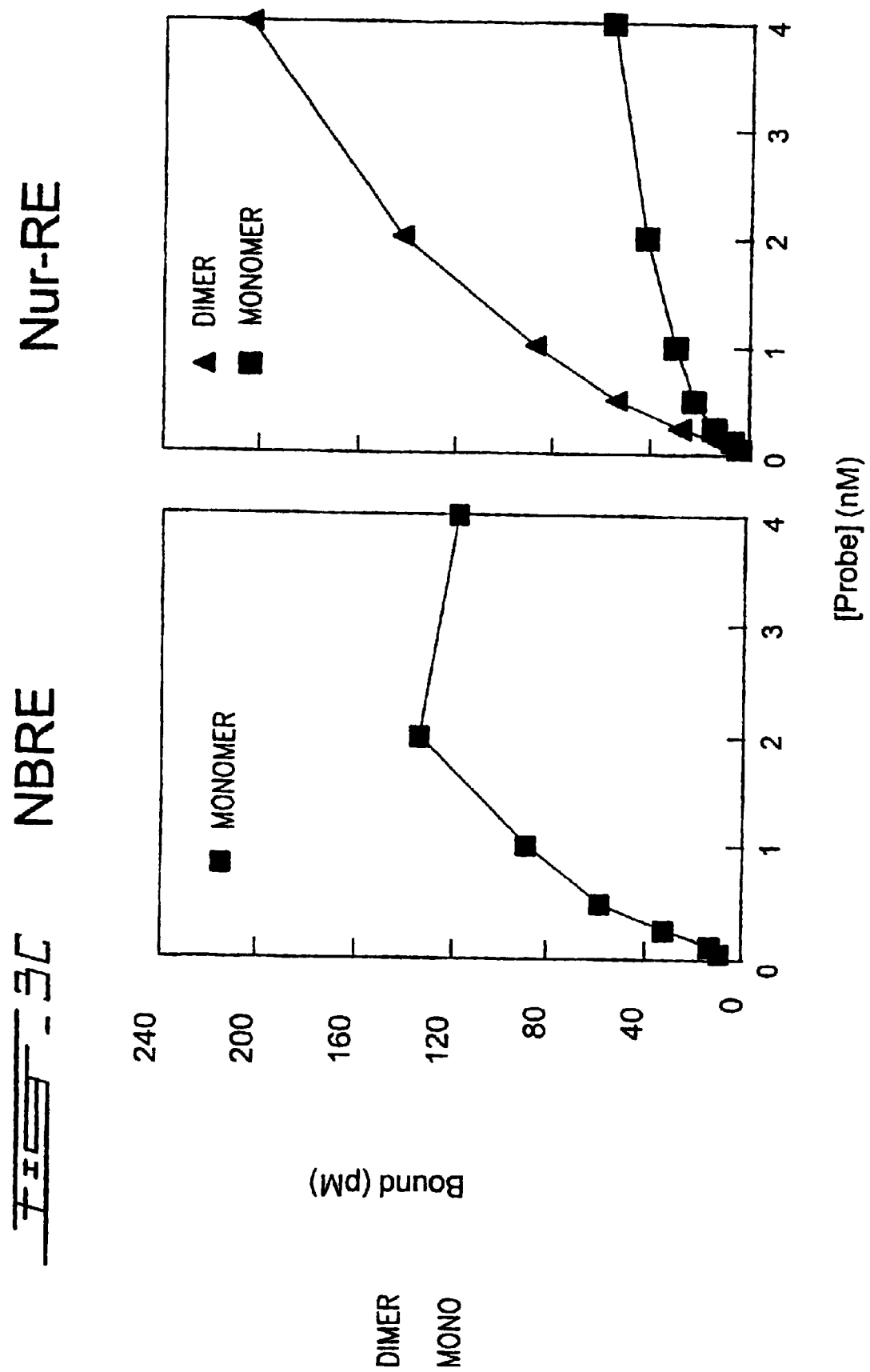

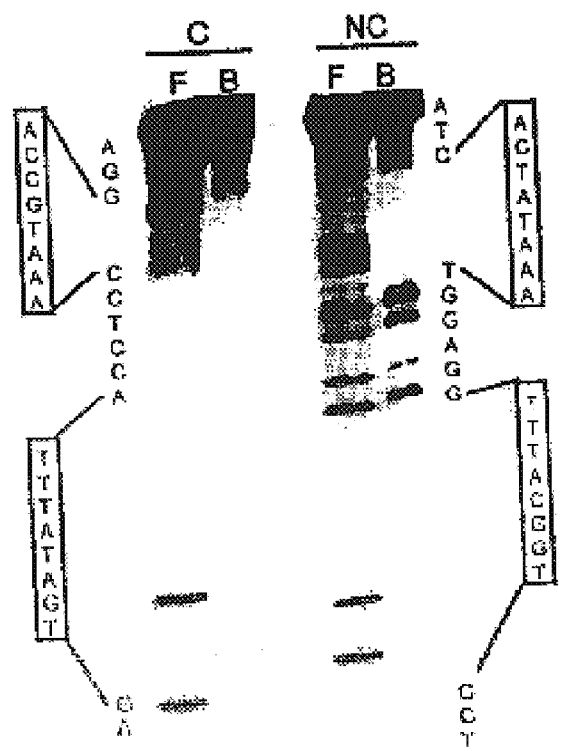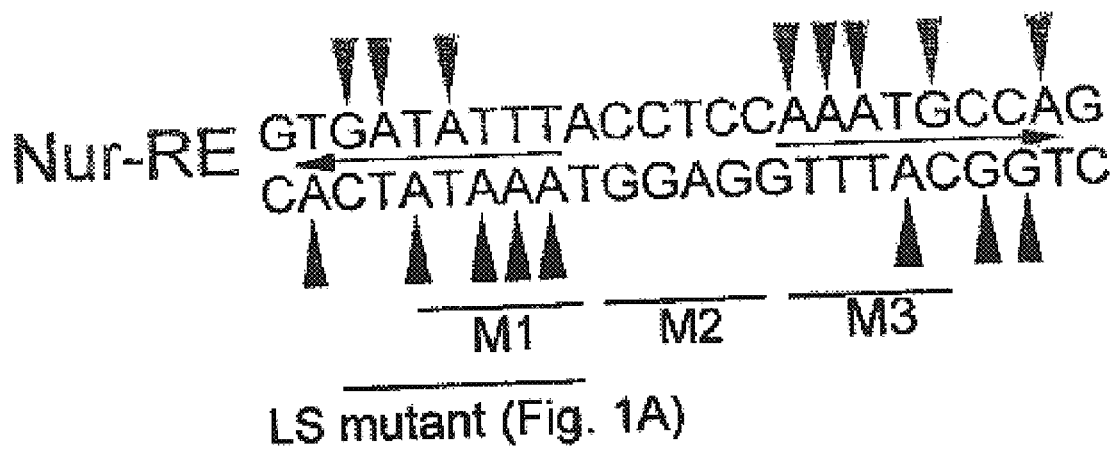
FIG. 3D

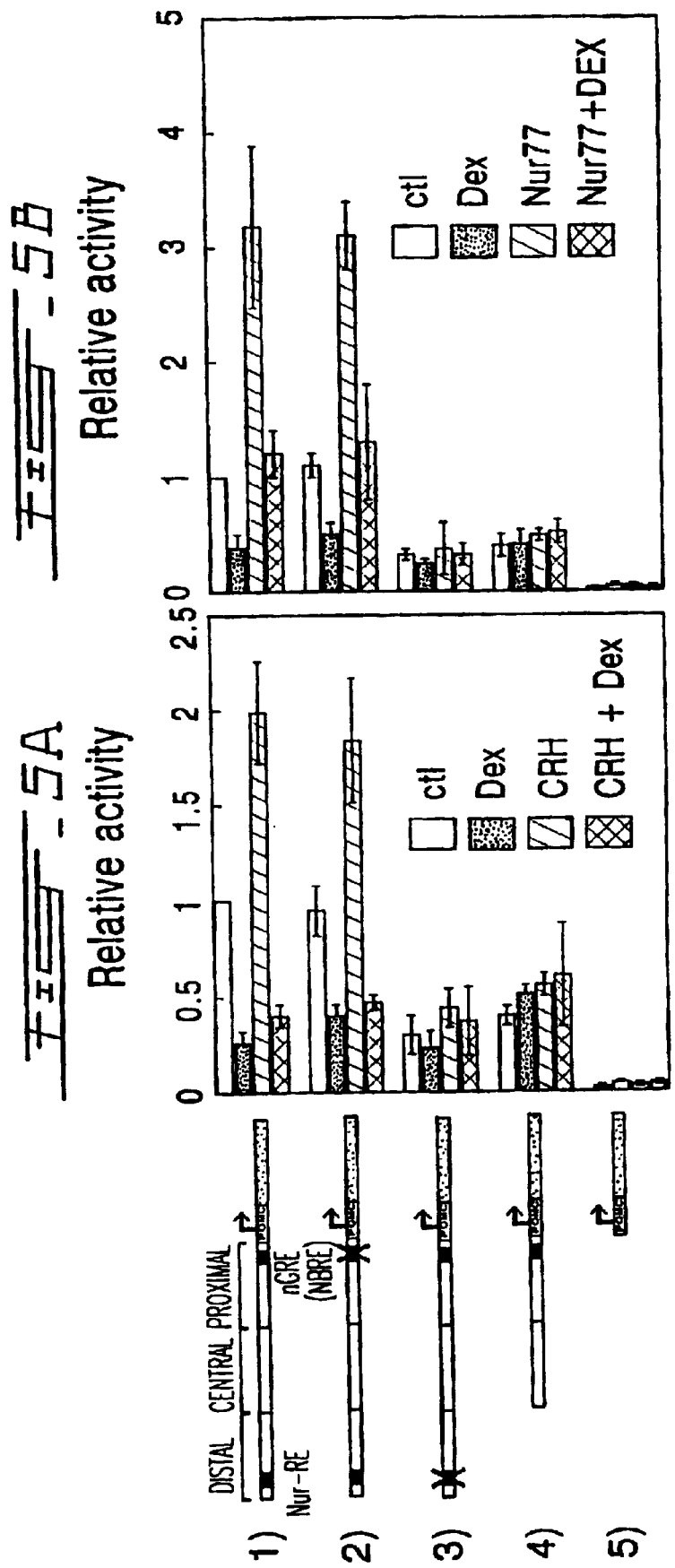

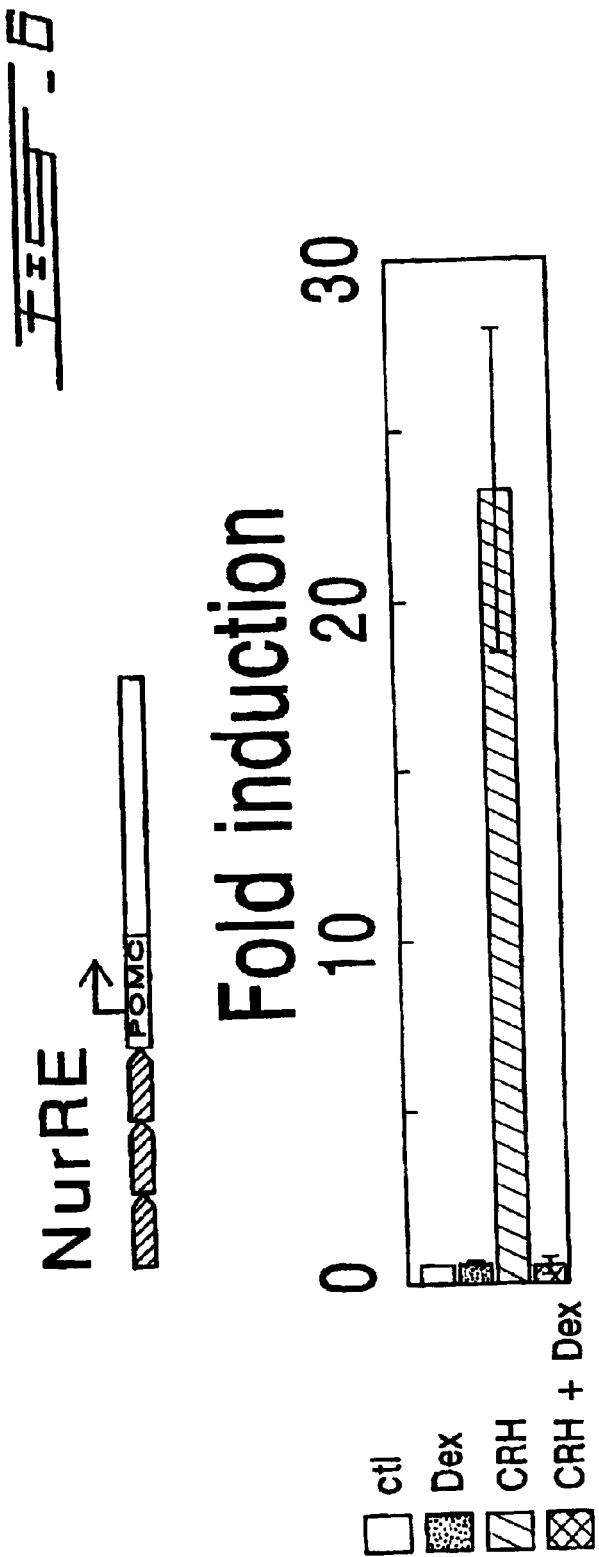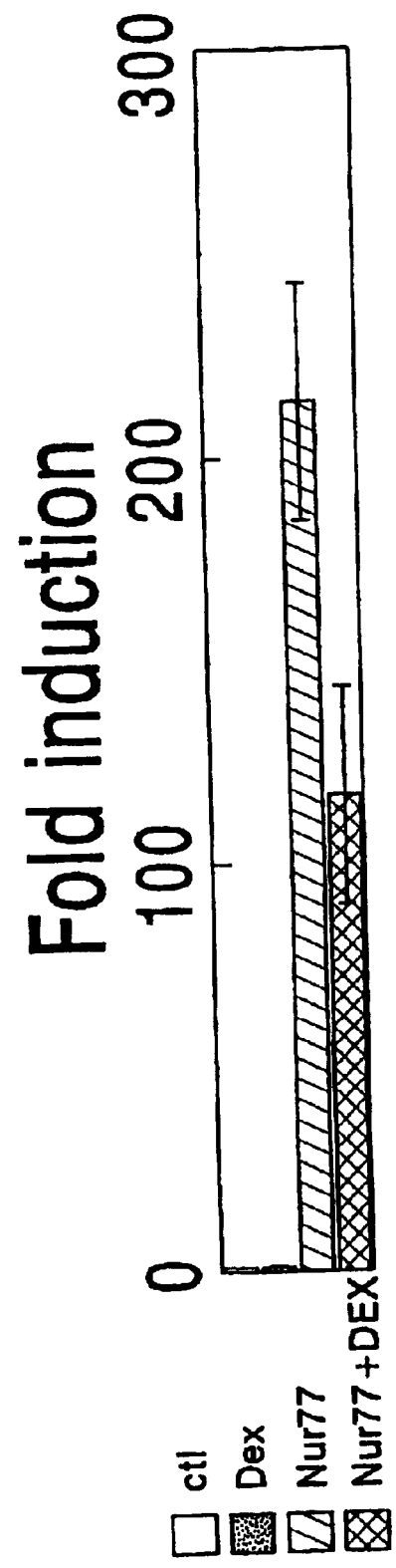
FIG. 6

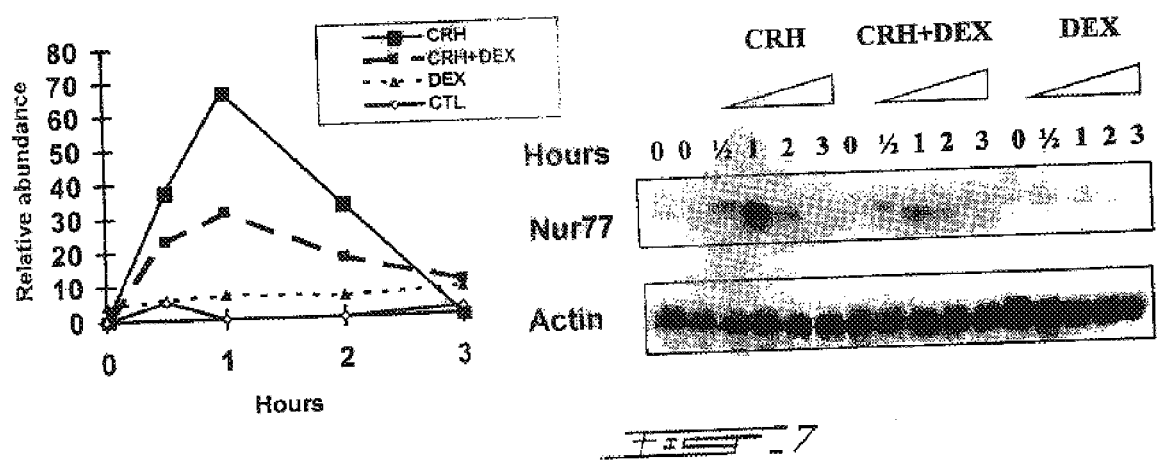

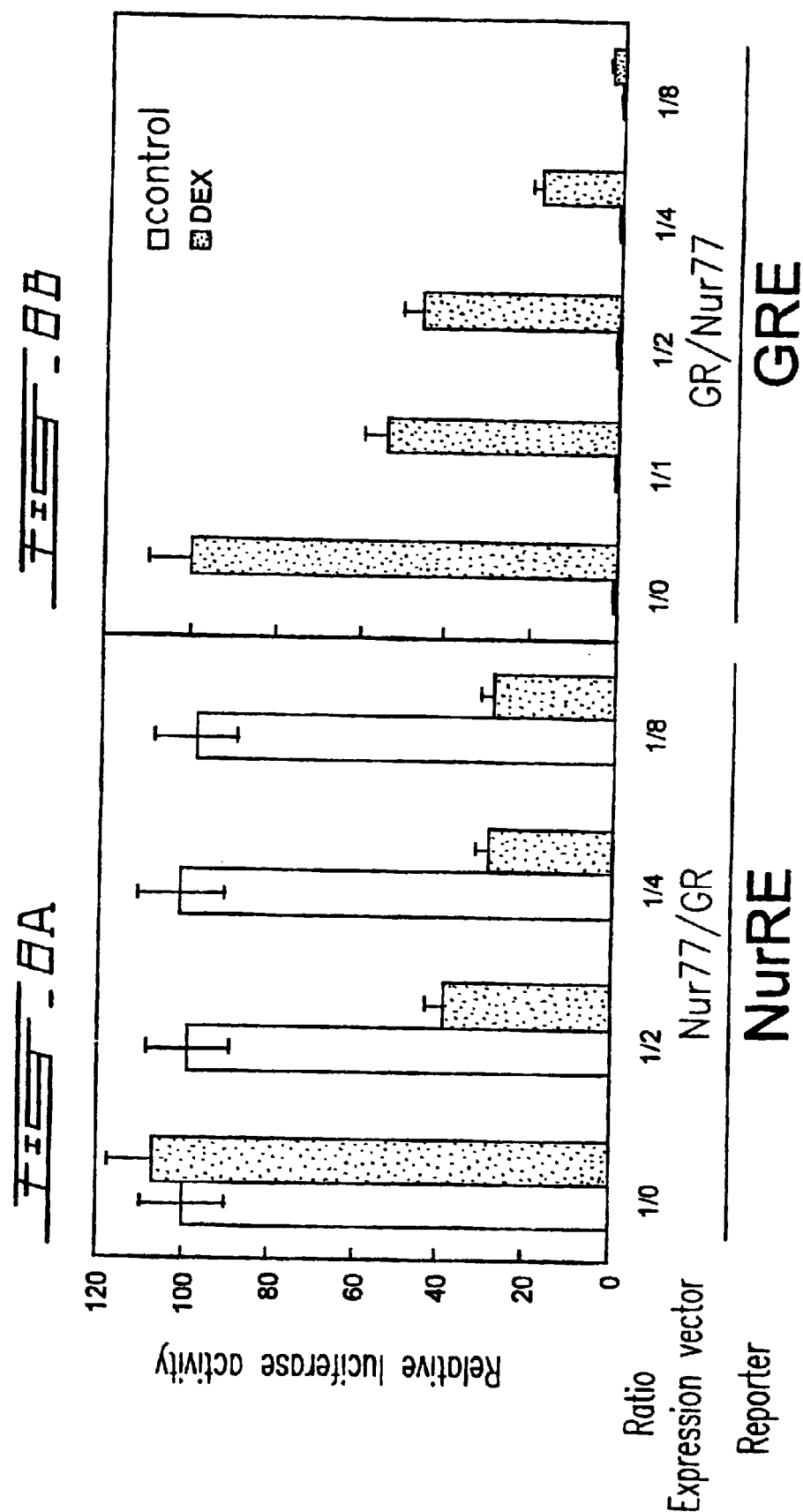

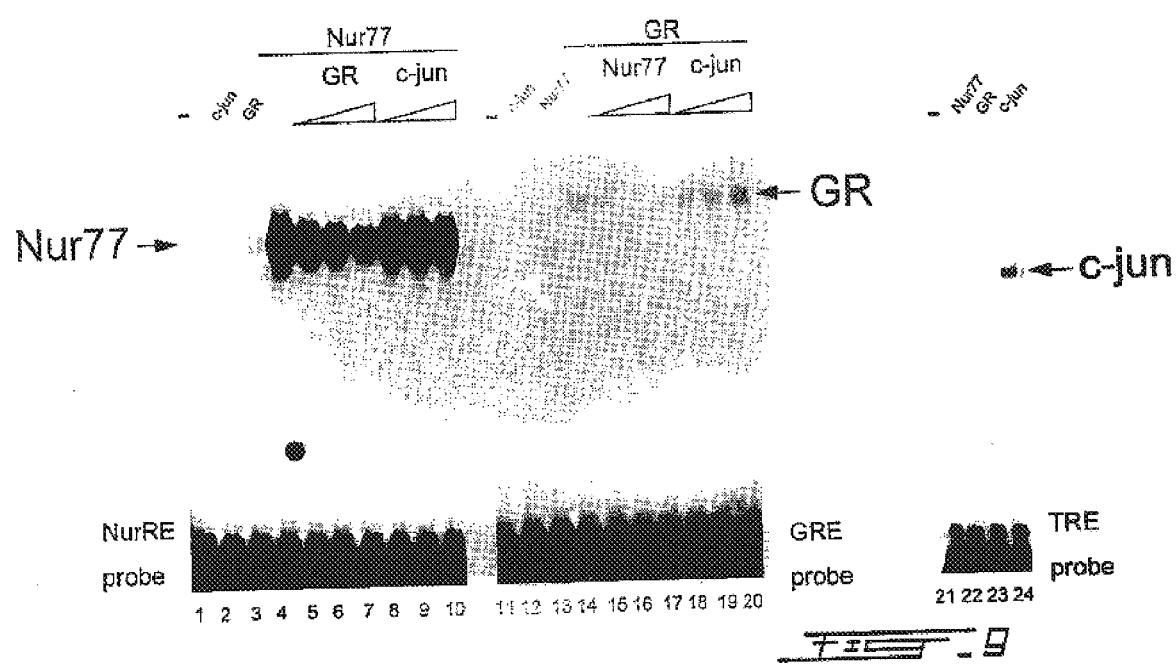

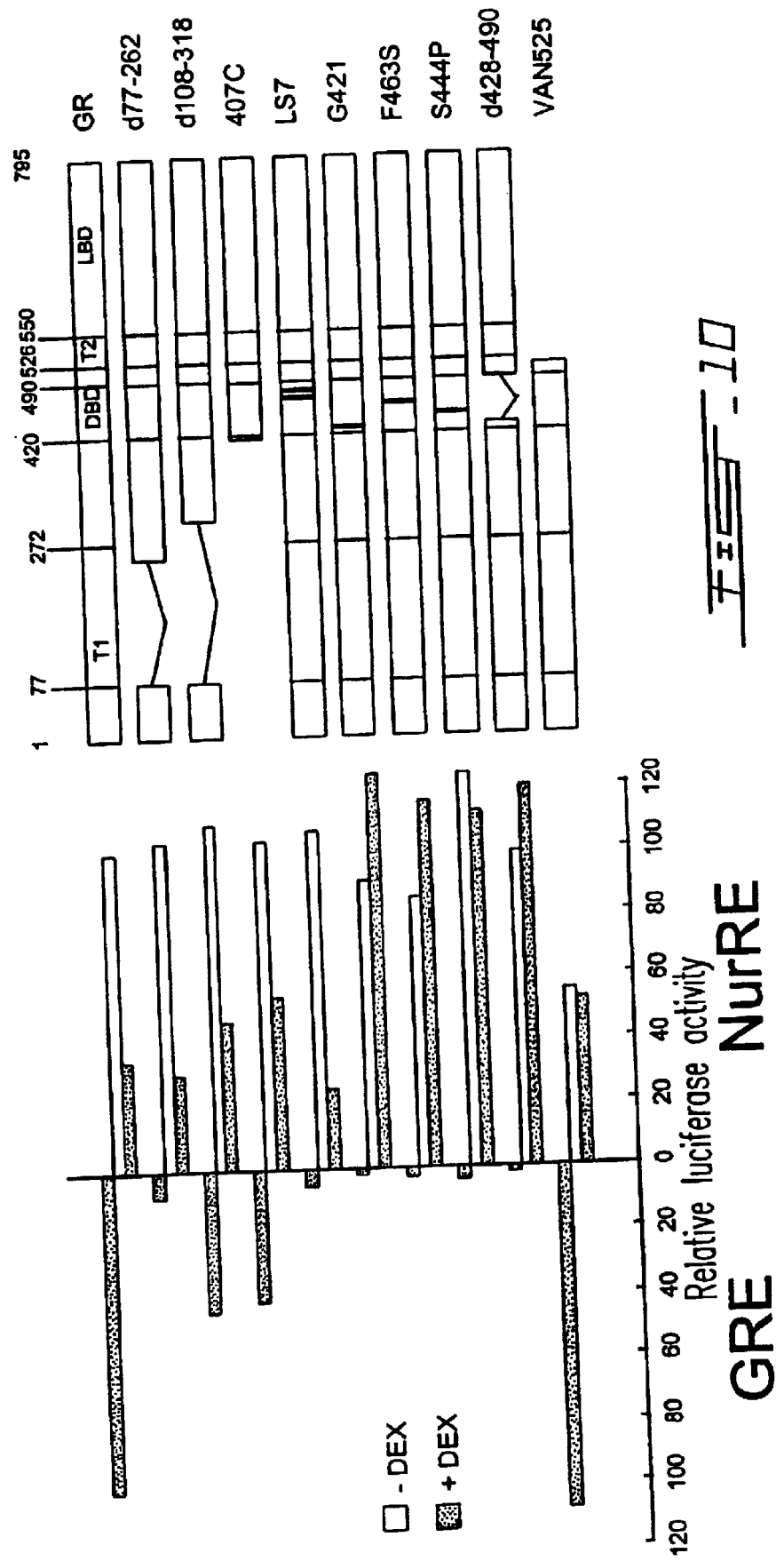
FIG_10

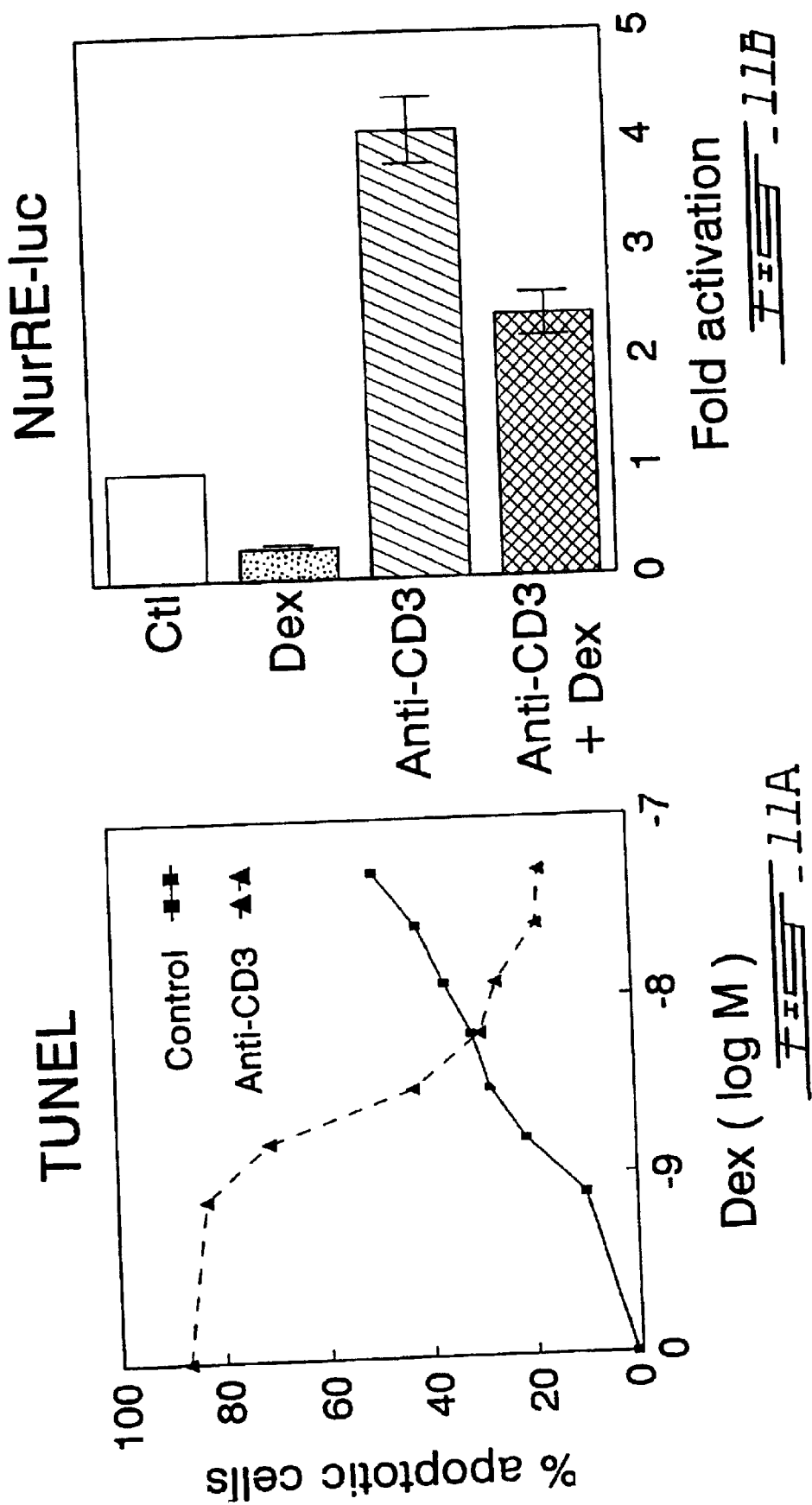

NUR-RE A RESPONSE ELEMENT WHICH BINDS NUR NUCLEAR RECEPTORS AND METHOD OF USE THEREFOR

STATEMENT REGARDING FEDERALLY SPONSORED RESEARCH OR DEVELOPMENT

This invention was made with government support under grant 1R01BK48070-01 awarded by the National Institutes of Health USA. The U.S. government has certain rights in the invention.

FIELD OF THE INVENTION

The present invention relates to intracellular receptors, and methods for the modulation of transcription using same. More particularly, the invention relates to the Nur family of nuclear receptors. In general aspects, the present invention relates to the identification of a physiologically relevant response element (RE) for Nur family members, as well as to the identification of the type of protein protein interactions of Nur family members, enabling their specific interaction with this RE and their modulation of transcription at physiologically relevant sites. The invention further relates to methods for modulating processes mediated by such nuclear receptors. In addition, the invention relates to oligonucleotide sequences that bind regulatory proteins that affect transcription, such as the Nur family of nuclear receptors, to DNA constructs comprising the oligonucleotide sequences, cells transfected with the DNA constructs, to methods of using same to provide for the controlled expression of heterologous genes, and for the detection and recovery of new regulatory proteins. The present invention further provides bioassays for the identification of compounds as potential agonists or antagonists of transcription by the Nur family of nuclear receptors. Moreover, the invention relates to the dissection of protein-protein interactions or ligand-protein interactions involved in the modulation of transcription by the Nur family of nuclear receptors.

BACKGROUND OF THE INVENTION

The Lipophilic hormones such as steroids, retinoids, and thyroid hormones can permeate a target cell and through their interaction with nuclear receptors, modify gene expression. Cloning and characterization of such receptors has shown that the binding of hormone to its receptor triggers an allosteric change thereof which in turns enables the hormone-receptor complex to specifically interact with a DNA target and modulate transcription. It is now widely recognized that these receptors are actually part of a superfamily of structurally related nuclear receptors which interact with chemically distinct ligands to directly affect gene expression. The importance of the nuclear receptor superfamily in maintenance of homeostasis and physiology of cells and organisms is demonstrated by the high level of conservation throughout evolution of the more than 150 members already characterized.

The nuclear receptors are characterized by (1) a DNA binding domain (DBD), responsible for the targeting of receptors to their specific response elements (RE); and (2) a ligand-binding domain (LBD), which ensures the specificity, selectivity and affinity of the binding of the ligand to its receptor (For reviews see, Mangelsdorf et al., 1995, Cell 83: 835–839; and Ibid 841–850). Characterization of the RE has shown that the RE consists of a core half-site defined by a degenerate Xn-AGGTCA which can be configured as direct repeats (DR), inverted repeats (IR), everted repeats (ER) or nonrepeats (NR) [PCT publication number WO96/21457 published Jul. 18, 1996]. Since the nuclear receptor recognize REs which are unique, it follows that subtle differences in the sequence of the RE or their configuration have significant effects on DNA binding of the receptor (Mangelsdorf et al., 1995, supra; and Ibid 841–850). Once bound to a RE, each receptor responds to its signal through the C-terminal ligand binding domain (LBD). The LBD contains several embedded subdomains which may include a C-terminal transactivation function, a series of heptad repeats which may serve as a dimerization interface and a poorly-delineated transcriptional suppression domain. In its natural context of the LBD, transcriptional activity through the transactivation domain, requires the addition of ligand (WO 96/21457).

A significant number of nuclear receptors are termed orphan receptors (no ligand which binds thereto has been identified). Such orphans have been identified by homology to the initial members of the superfamily in every metazoan species. It remains a significant challenge to identify a function for these orphan receptors, as well as to identify ligands and/or hormones that affect the activity thereof (Mangelsdorf et al., 1995, supra; and Ibid 841–850).

Nur77 (also known as NGFI-B, N10, NAK1, and TR3), was the first member of the Nur family of the orphan receptor subfamily of nuclear receptors to be identified. Other members of the Nur family include Nurr1 (for Nur-related member number one; also known as RNR-1, NOT and TINUR) and NOR-1 (also known as MINOR). Nur77 distinguishes itself by its ability to bind DNA as a monomer (Fahrner et al., 1991, Science 252:1296–1300; wilson et al., 1992, Science 256:107–110) and by its role in TCR-induced apoptosis in T cell (Liu et al., 1994, Nature 367:281–284; Woronicz et al., 1994, Nature 367:277–281; Calnan et al., 1995, Immunity 3:273–282). Of note, Nurr-1, the β isoform of Nur77 is described as a constitutively active orphan receptor that binds as a high-affinity monomer to an AA-AGGTCA core site and thus to the synthetic NBRE sequence (WO 96/21457). Indeed, WO 96/21457 teaches that Nurr-1 provides a well characterized example of the paradigms of binding of nuclear receptor as a monomer to a single core site.

Nur77 has been cloned repeatedly by numerous investigators either as a mitogen-inducible gene or as an immediate early gene (Hazel et al., 1988, Proc. Natl. Acad. Sci. USA 85:8444–8448; Milbrandt 1988, J. Neuron 1:183–188; Ryseck et al., 1989, EMBO J. 8:3327–3335; Nakai et al., 1990, J. Mol. Endocrinol. 4:1438–1443). Recent work has indicated that it is widely expressed, in particular throughout the brain.

Nur77 was shown to heterodimerize with RXR to confer 9-cis retinoic acid-dependent transcription (Perlmann et al., 1995, Genes Dev. 9:769–782; Forman et al., 1995, Cell 81:541–550) (WO 96/21457). Two common features of nonstemid receptors that have known ligands have been identified: the ligands are small lipophilic compounds and RXR Is part of the receptor complexes. Thus, orphan receptors such as Nur77 are likely candidates for ligand-dependent activation (Mangelsdorf et al., 1995, Cell 83: 841–850).

The experiments showing heterodimerization with RXR were carried out with two synthetic DNA elements: NBRE (Honkaniemi et al., 1994, Brain Res. 25:234–241)_(WO 96/21457) and DR-5 (Forman et al., 1995, supra). Synthetic NBRE was initially identified as a putative target for Nur77 by genetic selection in yeast (Fahrner et al., 1991, supra). Importantly in these experiments, Nur77 was shown to activate transcription as a monomer (Fahrner et al., 1991, supra; Wilson et al., 1992, supra; Mangelsdorf et al.,1995, supra).

There thus remains a need to identify physiological targets for the binding of Nur77 and related nuclear receptors. In addition, there remains a need to dissect the protein-protein interactions and ligand interactions relating to Nur77 and related nuclear receptors at their physiologically relevant target sites. More particularly, there remains a need to establish whether Nur family members modulate transcription as monomers and/or homodimers and/or heterodimers.

Glucocorticoids (Gc) and their receptors have been shown to repress transcription of target genes by Interaction of the Gc receptor (GR) with members of the AP-1 family of transcription factors (Jonat et al., 1990, Cell 62:1189–1204; Schüle et al., 1990, Cell 62:1217–1226; Yang-Yen et al., 1990. Cell 62:1205–1215). However, this mechanism does not account for repression of all Gc sensitive genes. This is the case of the Gc-repressed pro-opiomelanocortin (POMC) gene which encodes the precursor to ACTH, the major stimulus of adrenal Gc synthesis. Indeed, various mechanisms have been invoked to account for Gc repression of POMC transcription, including the formation of complexes containing three GR molecules on a negative Gc response element (nGRE) present at −63 bp in the POMC promoter (Drouin et al., 1993, EMBO J. 12:145–156). Some authors have suggested that a fos-dependent pathway may be involved in part but not exclusively (Boutillier et al., 1995, Mol. Endocrinol. 9:745–755) and others have implicated distal promoter sequences which are neither target for AP-1-related factors nor for GR (Riegel et al.,1991, Mol. Endocrinol.5:1973–1982).

There thus remain a need to identify the mechanism which accounts for GC repression of POMC transcription.

The present invention seeks to meet these and other needs.

The description found herein refers to a number of documents, the content of which is herein incorporated by reference.

SUMMARY OF THE INVENTION

This invention concerns a natural Nur77 target sequence or response element (RE) that is responsive to physiological stimuli in conditions where the NBRE is un—or poorly—responsive. Nur-RE is a novel response element configured as an ER-10 configuration. This novel Nur-response element (Nur-RE) mediates the physiological responses of the pro-opiomelanocortin (POMC) gene to CRH (Corticotropin Releasing Hormone) and its intracellular mediator CAMP. The Nur-RE (but not the NBRE, a single core sequence element) is also responsive to TCR-induced signals in T cell hybridomas.

In contrast to NBRE (SEQ ID NO: 3) binding by monomers, the Nur-RE binds homodimers of Nur77 and both halves of the Nur-RE are required for activity. Thus, the present invention is in contradistinction to the prior art which teaches that Nur-77 activates transcription as a monomer.

In accordance with the present invention, Nur-RE is shown to represent the only paradigm of Nur77, signaling that is physiologically responsive in both endocrine and lymphoid systems.

The instant invention is relevant not only to Nur77, but more broadly, to the Nur family of nuclear receptors which comprises at present Nurr-1 and NOR-1. Indeed, the instant invention is the first to also show a synergistic effect of heterodimeric complexes of different Nur family members on transcription through Nur-RE and related target sequences.

The present invention thus features multimeric or dimeric complexes comprising Nur family members. More particularly, it features homodimeric complexes comprising Nur family members. Even more particularly, it concerns Nur77 homodimers. The invention also features heterodimers complexes comprising different Nur family members as well as Nur family members and non-Nur nuclear receptors.

The invention also features the means to identify specific ligands of the Nur family members of orphan receptors.

Also, the invention features the means to identify factors that modulate the transcriptional activity of Nur family members through their interaction at Nur-RE and related target sequences. Such factors include, without being limited thereto, other nuclear receptors including Nur family members, and transcriptionally regulatory proteins.

The present invention also relates to a DNA construct comprising the NurRE or derivatives thereof, as part of an oligonucleotide (target sequence) operably linked to a promoter, which promoter is operably linked to a heterologous gene, wherein the DNA construct is linked in such a manner that the heterologous gene is under the transcriptional control of the oligonucleotide sequence and promoter. Also provided is a host cell transfected with such a DNA construct.

The present invention is also related to the use of the Nur-RE of the present invention and functional derivatives thereof to screen for agents that modulate gene expression of genes having a Nur-RE region or derivatives thereof in their control region. Such modulators can be used as lead compounds to design or search drugs that can modulate the level of expression of genes. Two non-limiting examples include the modulation of the level of gene expression of POMC and TCR-induced apoptosis in T cells.

The Nur-RE or derivatives thereof have utility in constructing in vitro or in vivo experimental models for studying Nur-RE dependent transcription modulation. Such experimental models make it possible to screen large collections of natural, semisynthetic, or synthetic compounds for therapeutic agents that affect Nur-RE-dependent transcription. Once identified an agent can be formulated in a pharmaceutically acceptable fashion such as described in PCT publication number WO/9829405, published Sep. 26, 1996, and documents cited therein.

The present invention further enables the identification of signalling pathways which converge at the Nur-RE or derivatives thereof.

The present invention also concerns a method for the controlled expression of a heterologous gene of interest comprising culturing the transfected host cells containing an appropriate Nur family member(s) in the presence of a compound. Preferably, the compound in this method comprises a suspected ligand and the Nur family member comprises Nur77. In another embodiment, the method comprises the use of other nuclear receptors such as RXR.

Further, the present invention concerns a method for measuring the ability of a compound to act as an agonist of gene transcription comprising (a) contacting the compound with a transfected host cell as described above under conditions in which the heterologous gene is capable of being expressed in response to the compound, and (b) comparing the level of gene expression in step (a) with the level of gene expression from the host cell in the absence of the compound. Alternatively, the present invention also concerns a method for measuring the ability of a compound to act as an antagonist of gene transcription. In both these methods, the heterologous gene may be any appropriate reporter gene such as the heterologous gene for luciferase, chloramphenicol acetyl transferase, green fluorescent protein, β-galactosidase and the like.

The invention further concerns ways to modulate the transcription of genes having Nur-RE target sequences or derivatives thereof. In a preferred embodiment, the present invention concerns a modulation of TCR-induced apoptosis. Such means to modulate transcription include, without being limited thereto, a targeting of the oligomerization domain (oligomerization promotion or inhibition) of Nur family members and a targeting of Nur-RE. More particularly, it concerns the dimerization domain of Nur family members.

In addition, the invention relates to methods to suppress the transcriptional activity of Nur family members comprising contacting same with excess amount of an oligonucleotide comprising Nur-RE.

The instant invention further relates to a method for identifying nuclear receptor(s) that oligomerize and/or dimerize (homo or hetero dimers) with Nur family members. Such method comprises introducing into a cell at least the DBD of a Nur family member, at least a portion of a nuclear receptor which putatively interacts with the Nur-family member, a reporter construct comprising Nur-RE or functional derivatives thereof, a promoter operable in the cell and a reporter gene, wherein the Nur-RE, promoter and reporter gene are operatively linked transcriptionally; and monitoring expression of the reporter upon expressive to the nuclear receptor. In a preferred embodiment Nur77 is used as the Nur-family member.

The invention further concerns methods for the identification of ligands which modulate transcription through a Nur family member(s) at a Nur-RE target sequence or functional derivative thereof, wherein such methods comprise the comparison of the level of reporter gene expression within cells, comprising a reporter gene construct, wherein the reporter gene is transcriptionally linked to Nur-RE or a functional derivative thereof, a Nur-family member(s), optionally another nuclear receptor, are exposed to a test compound and selecting those compounds which modulate only the relevant combinations.

Since different interactions among nuclear receptors can either restrict, redirect or lead to an acquision of new ligand binding phenotypes (WO 96/21457), the present invention provides a mean to dissect the type of interactions among receptors which is operated on a physiologically relevant DNA target for Nur-family members. For example, the effect of the interaction between a Nur-family member(s) and other nuclear receptor on the modulation of transcription by Nur-family member(s) with or without ligand can be evaluated. Similar dissections could be assessed at mutated Nur-RE target sites. Also, potentiation of the effect could be evaluated by modification of Nur-RE.

The applicant was the first to identify a natural response element for a Nur-family member of the nuclear receptor superfamily. The applicant indeed identified a previously undisclosed RE for Nur77 (ER-10). Moreover, the applicant herein demonstrates that contrary to what has been described in the literature, the monomeric and heterodimeric forms of transcription transactivators assumed by Nur family members, are not the only transcriptionally active forms thereof. Indeed, the applicant herein identifies homodimers of Nur77. Moreover, the homodimeric form of Nur77 is shown to be a physiologically relevant form of Nur transcriptional complexes on the genes tested. Using NBRE as a target site, Nur77 was shown to heterodimerize with retinoid X receptor (RXR), the complex thereby becoming responsive to 9-cisRA. The identification of a physiological target sequence for Nur77, now enables the assessment of the validity of the Nur77-RXR interaction thereon and opens the way to the dissection of relevant interactions relating to the control of gene expression through the Nur family of nuclear receptors. Indeed, the applicant has surprisingly discovered that the Nur-RE dependent action of Nur77 is not activated by 9-cisRA, in the presence or absence of RXR.

It will be clear that the instant invention is not limited to Nur77, as evidenced by the demonstration of a Nur-RE luciferase activation upon addition of Nur77, and/or Nurr-1, and/or NOR-1. It shall be understood that isoforms of these Nur family members may be used using the same principle taught herein. As evidenced by the present invention the Nur family members or isoforms thereof transactivate transcription through Nur-RE by binding homodimers (as exemplified for Nur77, Nurr-1 and NOR-1) and as heterodimers as exemplified for Nur77+Nurr-1, Nur77+NOR-1 and Nurr-1+NOR-1 or other types of multimers on Nur-RE (ER-10) containing reporter target genes.

The same principle applies Nur-RE. As demonstrated hereinbelow, and as known to the skilled artisan, oligonucleotide sequences can tolerate some changes without affecting their biological activity. As evidenced below, the Nur-RE can be mutated in the M2 region without affecting its physiologically relevant interaction with Nur77. Specific mutations of Nur-RE and a comparison of their effect on transcription modulation by Nur family members (using methods of the present invention) could permit a determination of a consensus sequence necessary and sufficient for specifically binding multimers comprising at least one member of the Nur family of nuclear receptors. Such a dissection could elucidate the intricate protein-protein and protein-DNA interactions occurring at different Nur response elements. As exemplified herein below a perfect palindromic Nur-RE was shown to be more active than the imperfect Nur-RE of POMC.

BRIEF DESCRIPTION OF THE DRAWINGS

In the appended drawings:

FIG. 5 shows that a NurRE mutation abrogates POMC promoter responsiveness to CRH and to Dex, as well as to overexpression of Nur77. A) The responsiveness of promoter constructs was tested in presence and absence of Dex $10^{-7}$M, CRH $10^{-7}$M or both. B) The responsiveness of the same promoter constructs to Dex and Nur77 overexpression was tested as indicated. The NurRE and nGRE mutations (indicated by an X on the diagrams at left) are transversions of 10 and 15 bp, respectively. The luciferase activity (average ± SEM of three experiments, each performed in duplicates) is shown relative to that of the full-length POMC promoter.

FIG. 6 shows the NurRE is entirely sufficient to confer responsiveness to CRH, Dex and Nur77. A) Responsiveness to CRH ($10^{-7}$M) and Dex ($10^7$M) of a reporter construct (NurRE-luc) containing three copies of a 28 bp NurRE oligonucleotide inserted upstream of a minimal POMC promoter (−35 to +63 bp). B) Responsiveness of the same reporter to Nur77 overexpression and Dex.

FIG. 7 shows a Northern blot analysis of Nur77 mRNA present in AtT-20 cells before and after treatment with CRH $10^{-7}$M, Dex 10-7M or both for the indicated times. The intensity of Nur77 mRNA bands was quantitated by densitometry and is expressed in graph form relative to the intensity of the µactin signal detected by re-hybridization of the same blots.

FIG. 8 shows that Nur77 and GR antagonize each other's action on cognate target reporters. The ratio of Nur77 and GR expression vectors was varied as indicated in cotransfection experiments in CV-1 cells in order to assess the effect of excess GR on Nur77-dependent activation of the NurRE-luc reporter and to assess the effect of excess Nur77 on GR and Dex ($10^{-7}$M) dependent activation of a GRE-containing reporter (Drouin et al., 1993, supra). A) The Nur77 expression vector was used at 50 ng/dish whereas GR expression vector was varied from 100 to 400 ng/dish. B) Expression vectors were: 50 ng/dish for GR and varied from 50 to 400 ng/dish for Nur77.

FIG. 9 shows that Nur77 and GR impair each other's ability to bind their cognate DNA sequence. Gel retardation experiments (Drouin et al., 1993, supra; Yang-Yen et al., 1990, supra) were used to study the effect of in vitro translated proteins on DNA binding. The binding of Nur77 to the NurRE probe (lanes 4 to 10) mostly produced complexes containing homodimers of Nur77; the effect of similar amounts of GR (lanes 5 to 7) and c-jun (lanes 8 to 10) was assessed on the formation of these Nur77 complexes. Similar experiments were performed with GR using a GRE probe (lanes 14 to 20). The c-jun preparation used in these experiments was active in TRE probe binding (lane 24) and this probe was not bound by Nur77 (lane 22) and GR (lane 23). Similarly, c-jun (lane 2) and GR (lane 3) did not bind NurRE, and c-jun (lane 12) and Nur77 (lane 13) did not bind GRE.

FIG. 11 shows that the antiCD3 activation of NurRE-luc reporter is antagonized by glucocorticoids. A) Dose-response curve of Dex effect on apoptosis of DO11.10 cells as measured by the TUNEL assay (Sgonc et al., 1994, supra) in presence or absence of antiCD3. The antiCD3 was used at 1 μg/ml to coat dishes prior to seeding; this concentration was determined experimentally for optimal induction of apoptosis. B) After electroporation in DO11.10 T hybridoma cells, NurRE-luc reporter activity was measured after TCR cross-linking using the antiCD3 antibody in presence or absence of Dex ($10^{-7}$M).

Figure 1A:
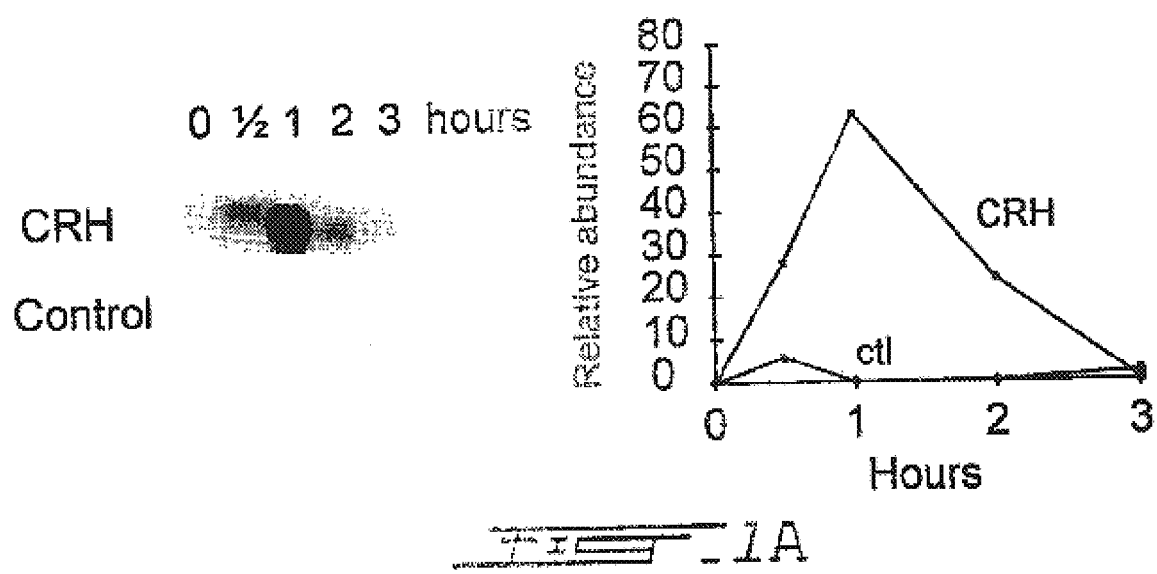
FIG. 1 shows that the POMC gene promoter contains a Nur response element (Nur-RE) that confers responsiveness to Nur77 and CRH in AtT-20 cells, and to TCR activation in T cell hybridomas. A) CRH ($10^{-7}$M) treatment of AtT-20 cells leads to a transient induction of Nur77 mRNA as assessed by Northern blot. Cellular β-actin mRNA was measured by hybridization on the same blot as control. Total AtT-20 cell RNA (20 μg) was used as previously described (Ohkura et al., 1994, Biochem. Biophys. Res. Commun. 205:1959–1965). B) Localizabon of Nur-RE and comparison of its activity with that of NBRE. The rat POMC promoter (−480 to +63 bp) fused to the luciferase reporter (construct 1) was previously described (Drouin et al., 1993, EMBO: J. 12:145–156). The mutations of the NBRE present within the nGRE (construct 2) and of Nur-RE (construct 3) contain transversions of 15 and 10 bp, respectively. Constructs 6 and 7 contain trimris of Nur-RE and NBRE (28 bp) inserted upstream of a minimal POMC promoter (−35 bp to +63 bp). C) Co-localization of CRH responsiveness with the Nur-RE. D) The Nur-RE confers responsiveness to both Nur77 overexpression and treatment with anti-CD3 in the T cell hybridoma DO 11.10.

Other objects, advantages and features of the present invention will become more apparent upon reading of the following non-restrictive description of preferred embodiments with reference to the accompanying drawings which are exemplary and should not be interpreted as limiting the scope of the present invention.

DESCRIPTION OF THE PREFERRED EMBODIMENT

The novel Nur response element of the present invention is a sequence which is related to the hexamer motif AGGTCA (SEQ ID NO: 3) of NBRE. Nur-RE is comprised of a half site which is an octomer sequence AAAGGTCA (SEQ ID NO: 1), in which the last 6 bp constitute the core hexamer motif used to classify the nuclear receptors.

In general, the abbreviations used herein for designating the amino acids are based on recommendations of the IUPAC-IUB Commission on Biochemical Nomenclature (Biochemistry, 1972, 11:1726–1732).

Unless defined otherwise, the scientific and technological terms and nomenclature used herein have the same meaning as commonly understood by a person of ordinary skill to which this invention pertains. Generally, the procedures for cell cultures, infection, molecular biology methods and the like are common methods used in the art. Such standard techniques can be found in reference manuals such as for example Sambrook et al. (1989, Molecular Cloning—A Laboratory Manual, Cold Spring Harbor Laboratories) and Ausubel et al. (1994, Current Protocols in Molecular Biology, Wiley, N.Y.).

Nucleotide sequences are presented herein by single strand, in the 5' to 3' direction, from left to right, using the one letter nucleotide symbols as commonly used in the art and in accordance with the recommendations of the IUPAC-IUB Biochemical Nomenclature Commission.

The present description refers to a number of routinely used recombinant DNA (rDNA) technology terms. Nevertheless, definitions of selected examples of such rDNA terms are provided for clarity and consistency.

As used herein, "isolated nucleic acid molecule", refers to a polymer of nucleotides. Non-limiting examples thereof include DNA and RNA molecules purified from their natural environment.

The term "recombinant DNA" as known in the art refers to a DNA molecule resulting from the joining of DNA segments. This is often referred to as genetic engineering.

The term "DNA segment", is used herein, to refer to a DNA molecule comprising a linear stretch or sequence of nucleotides. This sequence when read in accordance with the genetic code, can encode a linear stretch or sequence of amino acids which can be referred to as a polypeptide, protein, protein fragment and the like.

The nucleic acid (i.e. DNA or RNA) for practicing the present invention may be obtained according to well known methods.

As used herein, the term "physiologically relevant" is meant to describe interactions which can modulate transcription of a gene in its natural setting.

The term "oligonucleotide" or "DNA" molecule or sequence refers to a molecule comprised of the deoxyribonucleotides adenine (A), guanine (G), thymine (T) and/or cytosine (C), in a double-stranded form, and comprises or includes a "regulatory element" according to the present invention, as that term is defined herein. The term "oligonucleotide" or "DNA" can be found in linear DNA molecules or fragments, viruses, plasmids, vectors, chromosomes or synthetically derived DNA. As used herein, particular double-stranded DNA sequences may be described according to the normal convention of giving only the sequence in the 5' to 3' direction. "Regulatory element" refers to a deoxyribonucleotide sequence comprising the whole, or a portion of, an oligonucleotide sequence to which an activated transcriptional regulatory protein, or a complex comprising one or more activated transcriptional regulatory proteins, binds so as to transcriptionally modulate the expression of an associated gene or genes, including heterologous genes.

"Transcriptional regulatory protein" refers to cytoplasmic or nuclear proteins that, when activated, bind the regulatory elements/oligonucleotide sequences of the present invention either directly, or indirectly through a complex of transcriptional regulatory proteins or other adapter proteins, to transcriptionally modulate the activity of an associated gene or genes. Thus, transcriptional regulatory proteins can bind directly to the DNA regulatory elements of the present invention, or can bind indirectly to the regulatory elements by binding to another protein, which in turn binds to or is bound to a DNA regulatory element of the present invention. As used herein, transcriptional regulatory proteins, include, but are not limited to, those proteins referred to In the art as signal transducers and activators of transcription (STAT) proteins and nuclear receptors, as well as to all substantially homologous analogs and allelic variations thereof.

"Transcriptionally modulate the expression of an associated gene or genes" means to change the rate of transcription of such gene or genes.

The terms "vectors" or "DNA construct" are commonly known in the art and refer to any genetic element, including, but not limited to, plasmids, vectors, chromosomes, viruses and the like which can incorporate the oligonucleotide sequences, or sequences of the present invention and serve as DNA vehicle into which DNA of the present invention can be closed. Numerous types of vectors exist and are well known in the art The DNA construct can be a vector comprising a promoter that is operably linked to an oligonucleotide sequence of the present invention, which is in turn, operably linked to a heterologous gene, such as the gene for the luciferase reporter molecule. "Promoter" refers to a DNA regulatory region capable of binding directly or indirectly to RNA polymerase in a cell and initiating transcription of a downstream (3' direction) coding sequence. For purposes of the present invention, the promoter is bounded at its 3' terminus by the transcription initiation site and extends upstream (5' direction) to include the minimum number of bases or elements necessary to initiate transcription at levels detectable above background. Within the promoter will be found a transcription initiation site (conveniently defined by mapping with S1 nuclease), as well as protein binding domains (consensus sequences) responsible for the binding of RNA polymerase. Eukaryotic promoters will often, but not always, contain "TATA" boxes and "CCAT" boxes. Prokaryotic promoters contain Shine-Dalgarno sequences in addition to the −10 and −35 consensus sequences.

"Nucleic acid hybridization" refers generally to the hybridization of two single-stranded nucleic acid molecules having complementary base sequences, which under appropriate conditions will form a thermodynamically favored double-stranded structure. Examples of hybridization conditions can be found in the two laboratory manuals referred above (Sambrook et al., 1989, supra, and Ausubel et al., 1994, supra) and are commonly known in the art. In the case of a hybridization to a nitrocellulose filter, as for example in the well known Southern blotting procedure, a nitrocellulose filter can be incubated overnight at 65° C. with a labeled probe in a solution containing 50% formamide, high salt (5×SSC or 5×SSPE), 5×Denhardt's solution, 1% SDS, and 100 µg/ml denatured carried DNA (i.e. salmon sperm DNA). The non-specifically binding probe can then be washed off the filter by several washes in 0.2×SSC/0.1% SDS at a temperature which is selected in view of the desired stringency: room temperature (low stringency), 42° C. (moderate stringency) or 65° C. (high stringency). The selected temperature is based on the melting temperature (Tm) of the DNA hybrid. Of course, RNA-DNA hybrids can also be formed and detected. In such cases, the conditions of hybridization and washing can be adapted according to well known methods by the person of ordinary skill. Stringent conditions will be preferably used (Sambrook et al.,1989, supra).

As used herein, the term "gene" is well known in the art and relates to a nucleic add sequence defining a single protein or polypeptide. A "structural gene" defines a DNA sequence which is transcribed into RNA and translated into a protein having a specific amino acid sequence thereby giving rise the a specific polypeptide or protein.

A "heterologous" (i.e. a heterologous gene) region of a DNA molecule is a subsegment segment of DNA within a larger segment that is not found in association therewith in nature. The term "heterologous" can be similarly used to define two polypeptidic segments not joined together in nature. Non-limiting examples of heterelogous genes include reporter genes such as luciferase, chloramphenicol acetyl transferase, β-galactosidase, and the like which can be juxtaposed or joined to heterologous control regions or to heterologous polypeptides.

The term "vector" is commonly known in the art and defines a plasmid DNA, phage DNA, viral DNA and the like, which can serve as a DNA vehicle into which DNA of the present invention can be cloned. Numerous types of vectors exist and are well known in the art.

The term "expression" defines the process by which a structural gene is transcribed into mRNA (transcription), the mRNA is then being translated (translation) into one polypeptide (or protein) or more.

The terminology "expression vector" defines a vector or vehicle as described above but designed to enable the expression of an inserted sequence following transformation into a host. The cloned gene (inserted sequence) is usually placed under the control of control element sequences such as promoter sequences. The placing of a cloned gene under such control sequences is often referred to as being operably linked to control elements or sequences.

Operably linked sequences may also include two segments that are transcribed onto the same RNA transcript. Thus, two sequences, such as a promoter and a "reporter sequence" are operably linked if transcription commencing in the promoter will produce an RNA transcript of the reporter sequence. In order to be "operably linked" it is not necessary that two sequences be immediately adjacent to one another.

Expression control sequences will vary depending on whether the vector is designed to express the operably linked gene in a prokaryotic or eukaryotic host or both (shuttle vectors) and can additionally contain transcriptional elements such as enhancer elements, termination sequences, tissue-specificity elements, and/or translational initiation and termination sites.

Prokaryotic expression are useful for the preparation of large quantities of the protein encoded by the DNA sequence of interest. This protein can be purified according to standard protocols that take advantage of the intrinsic properties thereof, such as size and charge (i.e. SDS gel electrophoresis, gel filtration, centrifugation, ion exchange chromatography . . . ). In addition, the protein of interest can be purified via affinity chromatography using polyconal or monoclonal antibodies. The purified protein can be used for therapeutic applications.

A host cell or indicator cell has been "transfected" by exogenous or heterologous DNA (e.g. a DNA construct) when such DNA has been introduced inside the cell. The transfecting DNA may or may not be Integrated (covalently linked) Into chromosomal DNA making up the genome of the cell. In prokaryotes, yeast, and mammalian cells for example, the transfecting DNA may be maintained on an episomal element such as a plasmid. With respect to eukaryotic cells, a stably transfected cell is one in which the transfecting DNA has become integrated into a chromosome so that it is inherited by daughter cells through chromosome replication. This stability is demonstrated by the ability of the eukaryotic cell to establish cell lines or clones comprised of a population of daughter cells containing the transfecting DNA. Transfection methods are well known in the art (Sambrook et al., 1989, supra; Ausubel et al., 1994, supra). The use of a mammalian cell as indicator can provide the advantage of furnishing an intermediate factor, which permits for example the interaction of two polypeptides which are tested, that might not be present in lower eukaryotes or prokaryotes. Of course, an advantage might be rendered moot if both polypeptide tested directly interact. It will be understood that extracts from mammalian cells for example could be used in certain embodiments, to compensate for the lack of certain factors.

The oligonucleotide sequences of the present invention can also comprise multimers of two or more "units" of the basic regulatory elements. In this regard, such muftimer oligonucleotide sequences can, as a practical matter, contain from about 2 to 15 units of the same or different regulatory elements according to the present invention. However, theoretically, there is no limit to the number of regulatory elements within such a multimer oligonucleotide sequence. Such multimeric oligonucleotide sequences are useful as probes for detecting, isolating and/or purifying transcriptional regulatory proteins and in particular Nur family members or factors that interact therewith. Further, when used in a DNA construct, including a promoter and heterologous gene, according to the present invention, a multimer of the regulatory elements can enhance the expression of the gene from the DNA construct in response to various molecules such as transcription factors, nuclear receptors, ligands, or compounds (i.e. antagonist).

The regulatory elements and/or oligonucleotide sequences of the present invention will also prove useful in detecting, isolating and purifying new transcriptional regulatory proteins that display binding specificity to the regulatory elements/oligonucleotide sequences of the present invention either directly or indirectly, through their interaction with factors specifically interacting with the RE/oligonucleotide sequences. Further, it is contemplated that these regulatory elements/oligonucleotide sequences will prove particularly useful in the discovery of novel proteins which modulate transcription through a direct or indirect interaction with the RE/oligonucleotides of the invention. In this regard, detection of such novel transcriptional regulatory proteins can be accomplished with the following technique. Techniques which can be used for such identification are know in the art and includes techniques described in PCT publication number WO 95128482 published Oct. 26, 1995 and citations found therein. Such techniques can be in vitro methods which comprise the use of extracts of the nucleus and cytoplasm of cells, electrophoretic mobility shift assays, and in vitro translations. In addition, they can also be in vivo methods, based on the use of suitable DNA constructs in accordance with the present Invention.

The regulatory elements/nucleotide sequences of the present invention can also serve as a "probe", similar to those used in a variety of nucleic acid detection systems well known in the art, except that the probes of the present invention are used to detect proteins, rather than a nucleic acid sequences, which specifically bind to the regulatory elements/oligonucleotide sequences of the present invention. DNA probes according to the present invention preferably include the regulatory elements alone, or as part of a longer oligonucleotide sequence of the present invention, labeled with a detectable label, such as a radioisotope, an enzyme, a fluorescent label, a chemical label, or a modified base. In addition, multimers of the oligonucleotide sequence of the present invention are also contemplated as probes.

Thus, the present invention provides a method for detecting the presence of novel transcriptional regulatory proteins in a sample. Such samples are preferably biological samples, including, but not limited to, cells, cell culture supematant, cell or tissue extracts, or particular fractions thereof, and other biological fluids such as blood, sera, urine, saliva, etc. Such regulatory proteins could also be detected from in vitro preparations thereof, such as for example in vitro translated proteins. Binding of the probe containing the regulatory elements/oligonucleotide sequences of the present invention to a transcriptional regulatory protein in the sample may be detected by any appropriate means known in the art. For example, direct or indirect, or competitive binding assays may be used. Once detected, the novel transcriptional regulatory protein can be separated and purified from the probe-protein complex by any of a variety of techniques well known to those of skill in the art.

In one embodiment, the regulatory element/ oligonucleotide sequence of the present invention is immobilized on a solid support or carrier. As used herein "solid phase carrier or support" refers to any support capable of binding the oligonucleotide sequences/DNA regulatory elements of the present invention. Methods for coupling nucleic acids to the solid phase, the solid phase substances useful in these methods, and the means for elution of the proteins from the bound ligand, are well known to those of skill in the art.

The recombinant DNA constructs in accordance with the present invention can be constructed using conventional molecular biology, microbiology, and recombinant DNA techniques well known to those of skill in the art (i.e. Sambrook et al, 1989, Molecular Cloning: A Laboratory Manual). With a suitable DNA construct transfected into a host cell, the present invention provides a method for the controlled expression of a gene of interest. Alternatively, when the DNA construct comprises a reporter sequence, such as the gene for luciferase, transfection of the DNA construct into a host cell provides a convenient means for measuring the transcriptional activity of a reporter product in response to a signaling molecule, to a suspected ligand or to the presence of transcriptional factors or transcriptional modulators.

The term "ligand" is used herein in a broad sense and is intended to include natural ligands, synthetic ligands, and mixture of natural and synthetic ligands. The term "ligand" is also meant to cover a mixture of more than one ligand such as for example pools or libraries of molecules. Non-limiting examples of ligands include chemicals, biological macromolecules, cell extracts and the like. The terms "molecule" and "compounds" are used herein interchangeably with ligand and are similarly defined. The term "ligand"therefore denotes for examples macromolecules, cell or tissue extracts (from plants or animals). Non-limiting examples of ligands include nucleic acid molecules, peptides, antibodies, carbohydrates and pharmaceutical agents. The ligands can be selected and screened by a variety of means including random screening, rational selection and by rational design using for example protein or ligand modeling methods such as computer modeling. The terms "rationally selected" or "rationally designed" are meant to define compounds which have been chosen based on the configuration of the interaction domains of the present invention. As will be understood by the person of ordinary skill, macromolecules having non-naturally occurring modifications are also within the scope of the term "ligand". For example, peptidomimetics, well known in the pharmaceutical industry and generally referred to as peptide analogs can be generated by modeling as mentioned above. Similarly, in a preferred embodiment, the polypeptides of the present invention are modified to enhance their stability. It should be understood that in most cases this modification should not after the biological activity of the interaction domain. The molecules identified in accordance with the teachings of the present invention have a therapeutic value in diseases or conditions in which the physiology or homeostasis of the cell and/or tissue is compromised by a defect in transcription regulation at Nur-RE containing control regions and/or dependent on Nur family members and interacting factors (i.e. GR). The nucleic acid sequences and polypeptides of the present invention also find utility in the design of expression vectors.

As used herein, the term "selectable marker" is used broadly to refer to markers which confer an identifiable trait to the indicator cell. Non-limiting example of selectable markers include markers affecting viability, metabolism, proliferation, morphology and the like.

As used herein the recitation "indicator cells" refers to cells that express a Nur family member, fragment or variant thereof which can interact with another Nur family member to activate transcription at Nur-RE or derivatives thereof and another Nur family member, fragment or variant thereof and/or a glucocorticoid receptor (GR) or fragment thereof which can interact with a Nur family member, and wherein an interaction between these proteins or domains thereof is coupled to an identifiable or selectable phenotype or characteristic such that it provides an assessment of the interaction between the domains. Such indicator cells can be used in the screening assays of the present invention. In certain embodiments, the indicator cells have been engineered so as to express a chosen derivative, fragment, homolog, or mutant of Nur-Nur and/or Nur-GR interacting domains. The cells can be yeast cells or higher eukaryotic cells such as mammalian cells (WO 96/41169). Preferably, the indicator cells are mammalian cells. Non-limiting examples of such cells and vectors are exemplified herein below. In one particular embodiment, the indicator cell is a yeast cell harboring vectors enabling the use of the two hybrid system technology, as well known in the art (Ausubel et al., 1994, supra) and can be used to test a compound or a library thereof. In one embodiment, a reporter gene encoding a selectable marker or an assayable protein can be operably linked to a control element such that expression of the selectable marker or assayable protein is dependent on the interaction of the Nur-Nur and/or Nur-GR interacting domains. Such an indicator cell could be used to rapidly screen at high-throughput a vast array of test molecules. In a particular embodiment, the reporter gene is luciferase or β-Gal.

It should be clear to the person of ordinary skill that in one embodiment, at least one of a Nur-Nur or Nur-GR interaction domain of the present invention may be provided as a fusion protein. The design of constructs therefore and the expression and production of fusion proteins are well known in the art (Sambrook et al., 1989, supra; and Ausubel et al., 1994, supra). In one preferred embodiment, both interaction domains are part of fusion proteins. In one such preferred embodiment, the fusions are a LexA-Nur77 (DNA-binding domain—Nur77; bait) and a B42-GR fusion (transactivator domain—GR; prey). In a particular embodiment, the LexA-Nur77 and B42-GR fusion proteins are expressed in a yeast cell also harboring a reporter gene operably linked to a LexA operator and/or LexA responsive element.

It will also be dear that the present invention can be practiced with fusion proteins in mammalian cells and the protein-protein interactions dissected by deletion, point mutation analysis and the like directly, on the physiologically relevant DNA target sequence (as exemplified herein). A similar approach can be used to dissect the complex molecular interactions (protein-protein and protein-DNA) which occur at the Nur-RE target sequence upon binding of Nur family members, fragments or variants thereof and/or GR fragments or variants thereof.

For certainty, it should be clear that the term "Nur" is meant to cover the family of nuclear receptors and the "Nur-RE" refers to the ER-10 type of target sequence and derivatives thereof which can be used in the methods and assay of the present invention.

Non-limiting examples of such fusion proteins according to the present invention Include hemaglutinin fusions, Gluthione-S-transferase (GST) fusions, HIS fusions, and Maltose binding protein (MBP) fusions. In certain embodiments, it might be beneficial to introduce a protease cleavage site between the two polypeptide sequences which have been fused. Such protease cleavage sites between two heterologously fused polypeptides are well known in the art.

In certain embodiments, it might also be beneficial to fuse the interaction domains of the present invention to signal peptide sequences enabling a secretion of the fusion protein from the host cell. Signal peptides from diverse organisms are well known In the art. Bacterial OmpA and yeast Suc2 are two non-limiting examples of proteins containing signal sequences. In certain embodiments, it might also be beneficial to introduce a linker (commonly known) between the interaction domain and the heterologous polypeptide portion. Such fusions proteins find utility in the assays of the present invention as well as for purification purposes, detection purposes and the like.

As used herein, agonists or antagonists of gene transcription, through the RE of the present invention, include compounds that intervene at any point within the signaling pathway from interaction between the signaling molecule and a cell surface or intracellular receptor through activation of one or more transcriptional regulatory proteins and binding of the same to DNA regulatory elements, the end result of which is modulation of gene transcription by Nur family members. Further, as used herein, agonists and antagonists of gene transcription also include potentiators of known compounds with such agonist or antagonist properties. They also Include compounds that may facilitate or impair dimerization of regulatory proteins in condition where dimerization is an important or essential event for modulation of gene expression. As well the include compounds which facilitate or impair the protein-DNA Interaction occurring at Nur-RE and derivatives and variants thereof.

Agonists can be detected by contacting the transfected host cell with a compound or mix of compounds and, after a fixed period of time, determining the level of gene expression (e.g. the level of luciferase produced) within the treated cells. This expression level can then be compared to the expression level of the reporter gene in the absence of the compound(s). The difference between the levels of gene expression, if any, indicates whether the compound(s) of interest agonize the activation of intracellular transcriptional regulatory proteins in an analogous fashion to a known agonist of transcription. Further, the magnitude of the level of reporter product expressed between the treated and untreated cells provides a relative indication of the strength of that compound(s) as an agonist of gene transcription via a transcriptional regulatory protein pathway. Alternatively, such a transfected host cell can be used to find antagonists of known agonists of transcription, utilizing host cells transfected with the DNA construct according to the present invention. In such an assay, the compound or compounds of interest are contacted with the host cell in conjunction with one or more known agonists held at a fixed concentration. The extent to which the compound(s) depress the level of gene expression in the host cell below that available from the host cell in the absence of compounds, but presence of the known agonist, provides an indication and relative strength of the antagonist properties of such compound(s).

Of course, the antagonistic effect of a molecule can also be determined in the absence of agonist, simply by comparing the level of expression of the reporter gene product In the presence and absence of the test molecule(s).

It shall be understood that the "in vivo" experimental model can also be used to carry out an "in vitro" assay. For example, cellular extracts from the indicator cells can be prepared and used in one of the aforementioned "in vitro" tests (i.e. in vivi binding).

For certainty, the sequences and polypeptides useful to practice the invention include without being limited thereto mutants, homologs, subtypes, alleles and the like. It shall be understood that generally, the sequences of the present invention should encode a functional (albeit defective) interaction domain. It will be clear to the person of ordinary skill that whether an interaction domain of the present invention, variant, derivative, or fragment thereof retains its function in binding to its partner can be readily determined by using the teachings and assays of the present invention and the general teachings of the art. The same applies to the Nur-RE sequences of the present invention.

As exemplified herein below, the interaction domains of the present invention can be modified, for example by in vitro mutagenesis, to dissect the structure-function relationship thereof and permit a better design and identification of modulating compounds. However, some derivative or analogs having lost their biological function of interacting with their respective interaction partner (Nur or GR) may still find utility, for example for raising antibodies. Such analogs or derivatives could be used for example to raise antibodies to the interaction domains of the present invention. These antibodies could be used for detection or purification purposes. In addition, these antibodies could also act as competitive or non-competitive inhibitor and be found to be modulators of Nur-Nur and/or Nur-GR and/or Nur-NuRE interaction and the like.

As used herein, the designation "functional derivative" denotes, in the context of a functional derivative of a sequence whether an nucleic acid or amino acid sequence, a molecule that retains a biological activity (either function or structural) that is substantially similar to that of the original sequence. This functional derivative or equivalent may be a natural derivatives or may be prepared synthetically. Such derivatives include amino acid sequences having substitutions, deletions, or additions of one or more amino acids, provided that the biological activity of the protein is conserved. The same applies to derivatives of nucleic acid sequences which can have substitutions, deletions, or additions of one or more nucleoodes, provided that the biological activity of the sequence is generally maintained. When relating to a protein sequence, the substituting amino add as chemico-physical properties which are similar to that of the substituted amino acid. The similar chemico-physical properties include, similarities in charge, bulkiness, hydrophobicity, hydrophyficity and the like. The term "functional derivatives" is intended to include "fragments", "segments", "variants", "analogs" or "chemical derivatives" of the subject matter of the present invention.

Thus, the term "variant" refers herein to a protein or nucleic acid molecule which is substantially similar in structure and biological activity to the protein or nucleic acid of the present invention.

The functional derivatives of the present invention can be synthesized chemically or produced through recombinant DNA technology. All these methods are well known in the art.

As used herein, "chemical derivatives" is meant to cover additional chemical moieties not normally part of the subject matter of the invention. Such moieties could affect the physico-chemical characteristic of the derivative (i.e. solubility, absorption, half life and the like, decrease of toxicity). Such moieties are exemplified in Remington's Pharmaceutical Sciences (1980). Methods of coupling these chemical-physical moieties to a polypeptide are well known in the art.

The term "allele" defines an alternative form of a gene which occupies a given locus on a chromosome.

As commonly known, a "mutation" is a detectable change in the genetic maternal which can be transmitted to a daughter cell. As well known, a mutation can be, for example, a detectable change in one or more deoxyribonucleotide. For example, nucleotides can be added, deleted, substituted for, inverted, or transposed to a new position. Spontaneous mutations and experimentally induced mutations exist. The result of a mutations of nucleic acid molecule is a mutant nucleic acid molecule. A mutant polypeptide can be encoded from this mutant nucleic add molecule.

As used herein, the term "purified" refers to a molecule having been separated from a cellular component. Thus, for example, a "purified protein" has been purified to a level not found in nature. A "substantially pure" molecule is a molecule that is lacking in all other cellular components.

In general, techniques for preparing antibodies (including monoclonal antibodies and hybridomas) and for detecting antigens using antibodies are well known in, the art (Campbell, 1984, In "Monoclonal Antibody Technology: Laboratory Techniques in Biochemistry and Molecular Biology", Elsevier Science Publisher, Amsterdam, The Netherlands) and in Harlow et al., 1988 (in: Antibody—A Laboratory Manual, CSH Laboratories). The present invention also provides polyconal, monoclonal antibodies, or humanized versions thereof, chimeric antibodies and the like which inhibit or neutralize their respective interaction domains and/or are specific thereto.

From the specification and appended claims, the term therapeutic agent should be taken in a broad sense so as to also include a combination of at least two such therapeutic agents. Further, the DNA segments, proteins, potypeptides, ligands, compounds, antibodies and the like according to the present invention can be introduced into individuals in a number of ways as well known to the person of ordinary skill. For example, erythropoietic cells can be isolated from the afflicted individual, transformed with a DNA construct according to the invention and reintroduced to the afflicted individual in a number of ways, including intravenous injection. Alternatively, the DNA construct can be administered directly to the afflicted individual, for example, by injection in the bone marrow. The DNA construct can also be delivered through a vehicle such as a liposome, which can be designed to be targeted to a specific cell type, and engineered to be administered through different routes.

For administration to humans, the prescribing medical professional will ultimately determine the appropriate form and dosage for a given patient, and this can be expected to vary according to the chosen therapeutic regimen (i.e DNA construct, protein, cells), the response and condition of the patient as well as the severity of the disease.

Composition within the scope of the present invention should contain the active agent (i.e. fusion protein, nucleic acid, and molecule) in an amount effective to achieve an inhibitory effect on HIV and related viruses while avoiding adverse side effects. Typically, the nucleic acids In accordance with the present invention can be administered to mammals (i.e. humans) In doses ranging from 0.005 to 1 mg per kg of body weight per day of the mammal which is treated. Pharmaceutically acceptable preparations and salts of the active agent are within the scope of the present invention and are well known in the art (Remington's Pharmaceutical Science, 16th Ed., Mack Ed.). For the administration of polypeptides, antagonists, agonists and the like, the amount administered should be chosen so as to avoid adverse side effects. The dosage will be adapted by the clinician in accordance with conventional factors such as the extent of the disease and different parameters from the patient. Typically, 0.001 to 50 mg/kg/day will be administered to the mammal.

Thus, the present invention concerns methods to assay for agonists and antagonists of gene transcription utilizing the regulatory elements/oligonucleotides of the present invention in appropriate DNA constructs and transfected host cells. Further, the agonist and antagonist compounds discovered utilizing these methods can serve as pharmaceutical agents in the intervention of various disease states and conditions, or to ameliorate disease states wherein a modulation of transcription would be beneficial, a non-limiting example thereof includes TCR-induced apoptosis.

Having herein identified dimers as a physiologically relevant modulator of transcription, the present invention provides means to modulate transcription by affecting dimerization (or other types of multimerization). For example, an inhibition of Nur77 dimerization could reverse the Nur77-dependent TCR-induced apoptosis in T cells. Alternatively, promoting dimerization could enhance this TCR-induced apoptosis. The discovery that Nur family members and glucocorticoids can interact to affect Nur-RE-dependent transcription opens the way to a modulation of therapeutic actions of glucocorticoids with the Nur-RE-dependent signalling pathway.

The present invention is described in further detail In the following non-limiting examples.

EXAMPLE 1

Transfections

Transfections in AtT-20 cells were performed by lipofection (lipofectin, Gibco) using exponentially growing AtT-20 cells ($7.5 \times 10^5$) in 35 mm Petri dishes. Cells were grown in DMEM with 10% fetal calf serum stripped with dextran-coated charcoal. Cells and media were harvested 16 h after lipofection. Each sample for lipofection contained a total of 1.5 µg DNA, including 300 ng reporter plasmid, 300 ng RSV-GH as internal control, 100 ng of pCMX-Nur77 expression vector, and total DNA was completed to 1.5 µg with pSP64. The POMC promoter constructs were described previously (Therrien et al., 1991, Mol. Cell. Biol. 11:3492–3503; Therrien et al., 1993, Cell. Biol. 13:2342–2353.). In particular, the NurRE and nGRE linker scanning replacement mutations were described previously as mutants 3 and 15 in a series of promoter mutations (Therrien et al., 1991, supra). DO 11.10 cells were electroporated using a Biorad instruments at 250 V, 960 µFarad, and 10 µg each of reporter plasmid and expression vectors. CRH ($10^{-7}$M) and forskolin ($10^{-7}$M) were used at maximally active concentrations, and anti-CD3 (clone 145-2C11) was used at 1 µg/ml to coat dishes. The expression plasmid for the Nur77 dominant negative mutant was used at 3 µg/dish. Data are presented as the means ± SEM of 3 to 5 experiments each performed in duplicate.

EXAMPLE 2

Gel Retardation

NBRE (5'-GATCCTCGTGCGAAAAGGTCAAGC GCTA-3') (SEQ ID NO: 4) or NurRE (5'-GATCCTAGTGATATTTACCTCCAAATGCCAGGA-3') (SEQ ID NO: 5) oligonucleotides were 3'-end-labeled using Klenow polymerase and purified on polyacrylamide gels. Binding conditions and DMS interference were as previously described (Drouin et al., 1993, EMBO J. 12:145–156; Drouin et al., 1992, Mol. Endocrinol. 6:1299–1309). Typically, about 10 ng in vitro translated Nur77 synthesized with the Promega TNT SP6/T7 kit, was used in gel retardation experiments.

EXAMPLE 3

A Nur-RE in the POMC Promoter

As Nur77 was previously implicated in regulation of the hypothalamo-pituitary-adrenal axis (Honkanlemi et al., 1994, supra; Parkes et al., 1993, Mil. Endocrinol. 7:1357–1367; Davis et al., 1994, Mol. Cell. Biol. 14:3469–3483), we tested whether it is induced in POMC-expressing cells in response to CRH and whether it acts on transcription on the POMC gene (FIG. 1). Nur77 expression is rapidly Induced in response to CRH (FIG. 1A). Overexpression of Nur77 was found to increase transcription of a POMC luciferase reporter (FIG. 1B, construct 1) and mutagenesis of a NBRE sequence [found within a previously described nGRE (Themen et al., 1991, supra)] did not prevent this effect (construct 2). However, deletion of the distal region of the promoter (Drouin et al., 1993, supra) was found to abolish activity (construct 4) and further mapping of the responsive sequences using a variety of deletions and linker scanning mutants (data not shown) led to the identification of a target sequence, the Nur-RE, centered around –395 bp. A specific linker scanning mutation of the Nur-RE abolished responsiveness to Nur77 (construct 3). In order to clearly define sequences required for Nur response, a Nur-RE oligonucleotide was inserted in three copies upstream of a minimal promoter, and this response element was found to confer high responsiveness to Nur77 (construct 6). In this context, the Nur-RE is at least 40 times more responsive than the NBRE (construct 7, note scale difference).

Since the Nur orphan receptors have been implicated in signaling (Liu et al., 1994, supra; Woronicz et al., 1994, supra; Honkaniemi et al., 1994, supra; Parkes et al., 1993, supra; Davis et al., 1994, supra; Chan et al., 1993, J. Neurosci. 13:5126–5138), we tested whether the stimulatory effect of CRH on POMC transcription might be mediated through this pathway. When the same promoter deletions were tested for responsiveness to CRH (FIG. 1C), it was found that the Nur-RE confers responsiveness to CRH as the linker scanning mutation of this element (FIG. 1, construct 3) abolished responsiveness to the hypothalamic hormone, and oligornerization of the response element leads to a greatly enhanced response (construct 6).

EXAMPLE 5

TCR Activation Targets Nur-RE in T Cells

In view of the importance of the Nur pathway in TCR-mediated signaling, we tested the relative activity of the Nur-RE and NBRE in T cell hybridomas following Nur77 expression and anti-CD3 activation of TCR signaling (FIG. 1D). Whereas the Nur-RE reporter was induced by TCR activation, the NBRE reporter was not. Thus, the Nur-RE provides a paradigm for naturally occurring target sequences of the Nur orphan receptor signaling pathway.

EXAMPLE 6

Dominant Negative Mutant of Nur77 Blocks the Action of CRH

Figure 2:
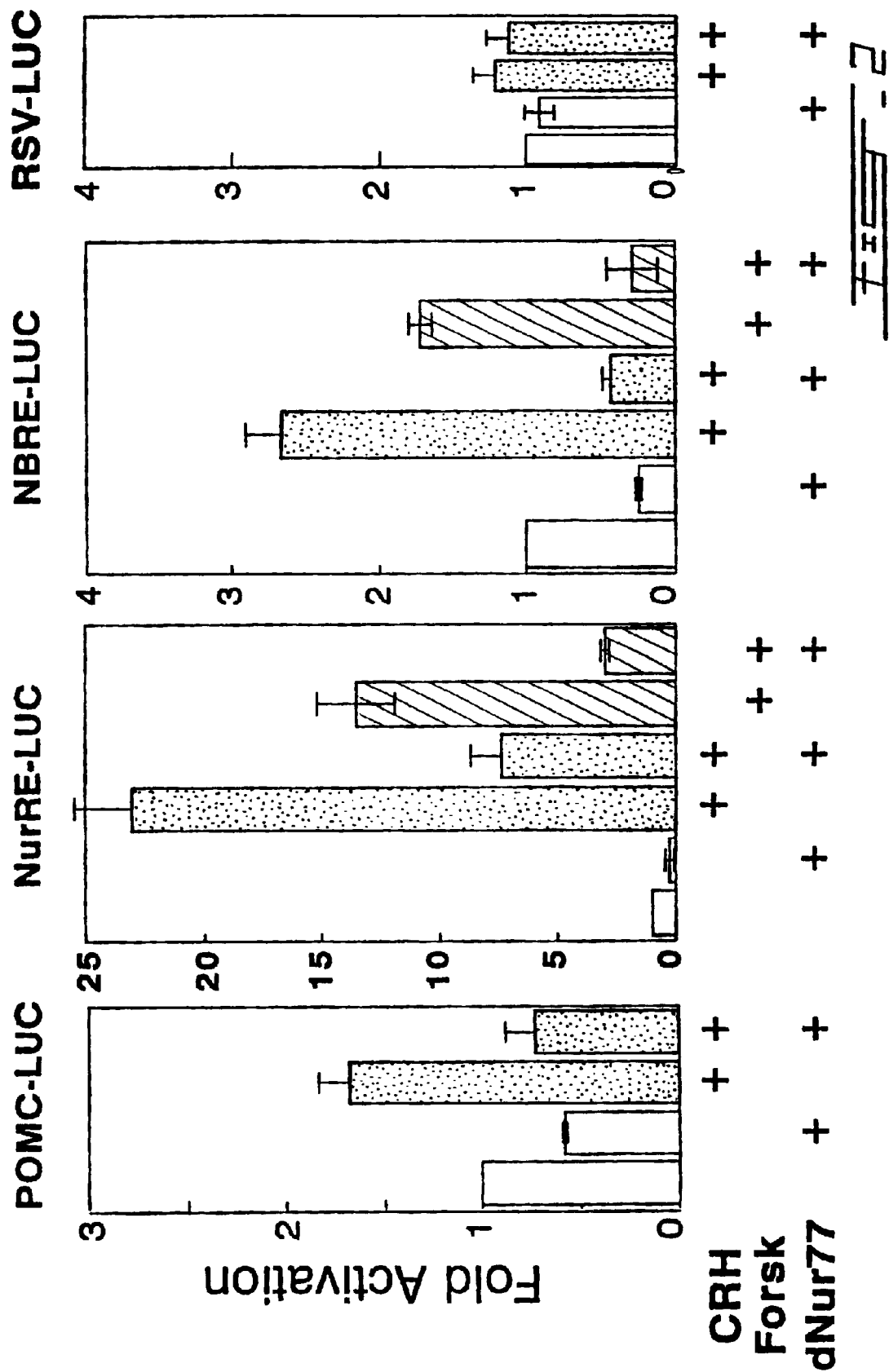
FIG. 2 shows a blockade of CRH and forskolin responsiveness by a dominant negative mutant of Nur77 (dNur77). The response of four reporter plasmids to CRH ($10^{-7}$M) and forskolin ($10^{-7}$M) was tested after lipofection in AtT-20 cells. The reporters were: POMC-luc, Nur-RE-luc, NBRE-luc, and RSV-luc as a negative control reporter. Lipofection was performed as described in the legend to FIG. 1 and the expression plasmid for the Nur77 dominant negative mutant was used at 3 µg/dish. This dominant negative mutant was described previously (Woronicz et al., 1994, supra) and shown to block TCR-induced apoptosis in T cells.

Since it was previously suggested that CRH may mediate its effect through CAMP and PKA, the response of the Nur-RE to forskolin was also tested (FIG. 2). Interestingly, the Nur-RE reporter was also responsive to forskolin but less so than to CRH, suggesting that CRH may induce other pathways In addition to the cAMP pathway. In order to demonstrate the importance of the Nur pathway in activation of the POMC promoter in response to CRH and cAMP, we used a dominant negative mutant of Nur77 (dNurr77) that had previously been shown to block TCR-induced signals and apoptosis in T cells (Woronicz et al., 1994, supra). Overexpression of dNur77 decreased basal POMC promoter activity and completely blunted CRH-induced activity (FIG. 2). In addition, dNurr77 blunted the response of the Nur-RE reporter to CRH and forskolin. The weak activity and responsiveness of the NBRE-containing reporter was also decreased by dNur77. The complete reversal of CRH-induced POMC transcription by dNur77 suggests that this pathway is solely responsible for the transcriptional actions of CRH in AtT-20 cells.

EXAMPLE 7

Nur-RE Binds Dimers of Nur77

Figure 3A:
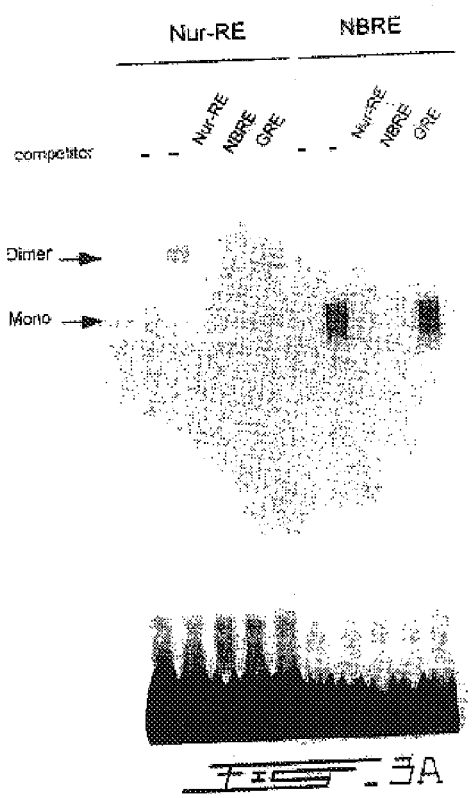
FIG. 3 shows the characterization of Nur-RE. A) Binding of in vitro translated Nur77 to Nur-RE and NBRE. The position of monomeric (mono) and dimeric (dimer) complexes is indicated by arrows. Competitor oligonucleotides were used at 100-fold molar excess. B) Binding curve of Nur77 in the presence of increasing concentrations of Nur-RE and NBRE. C) Quantitation of binding experiments shown in B. Each band was quantitated using phosphor-Imager™. D) Localization of Nur-RE by DMS interference. End-labeled coding (C) and non-coding (NC) strands of the Nur-RE were used for DMS interference of Nur77 binding. DMS methylation partially revealed A residues in addition to guanosine. Residues that interfere with binding are boxed on either sides of the gels, and they are indicated by arrowheads on the Nur-RE sequence below. Arrows between the strands indicate the position of the Nur-RE half-sites which are related to the consensus AAAGGTCA. The position of transversion mutations (M1, M2, M3) used in binding experiments shown in E is indicated below the sequence. In addition, nucleotides mutated in the linker scanning mutant used in FIG. 1B are indicated by a line. E) Binding of Nur77 to the wild-type and mutant Nur-RE. The position of each mutation is indicated below the sequence in D. F) Relative acidly of Nur-RE and mutants compared to that of NBRE. Lipofection was carried out as in FIG. 1B. The mutant Nur-RE has 2 bp replaced at positions −390/−391 in the POMC promoter (Therrien et al., 1991, Mol. Cell. Biol. 11:3492–3503). Methods. For gel retardation experiments, Nur-RE or NBRE oligonucleotides were 3'-end-labeled using Klenow polymerase and purified on polyacrilamide gels. Binding conditions and DMS interference were as previously described (Drouin et al., 1993, supra; Drouin et al., 1992, Mol. Endocrinol. 6:1299–1309)
Figure 3B:
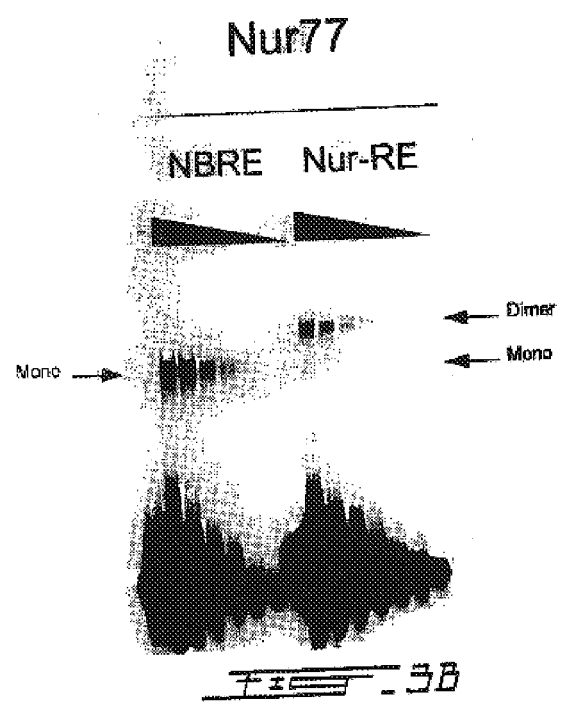

The interaction of Nur77 with Nur-RE was investigated directly in binding studies using in vitro translated Nur77. Surprisingly, these binding experiments indicated that the Nur-RE binds homodimers of Nur77 in contrast to the monomeric interaction of this receptor with NBRE (FIG. 3A). The prevalence of dimeric complexes in gel retardation experiments suggests that dimer formation is co-operative (FIG. 3B and C). In competition experiments, both Nur-RE and NBRE exhibited similar specificity of binding (FIG. 3A). The interaction of Nur77 with Nur-RE was further defined using the DMS interference method (FIG. 3D). This analysis indicated that two Nur77 moieties interact with octamer motifs that are found in an inverse orientation and separated by 6 bp. Each motif is loosely related to the NBRE: AAAGGTCA (SEQ ID NO: 1) (FIG. 3D). The upstream octamer motif is the most conserved by comparison to NBRE. The linker scanning mutation used to localize the Nur-RE (FIG. 1A, construct 3) was targeted to this upstream motif as indicated in FIG. 3D. However, this upstream motif is insufficient on its own to confer Nur-RE activity (see below).

EXAMPLE 8

Both Halves of Nur-RE are Required

Figure 3E:
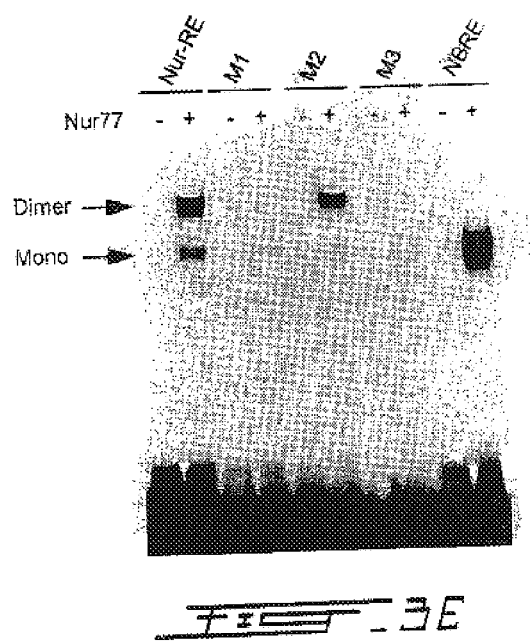
Figure 3F:
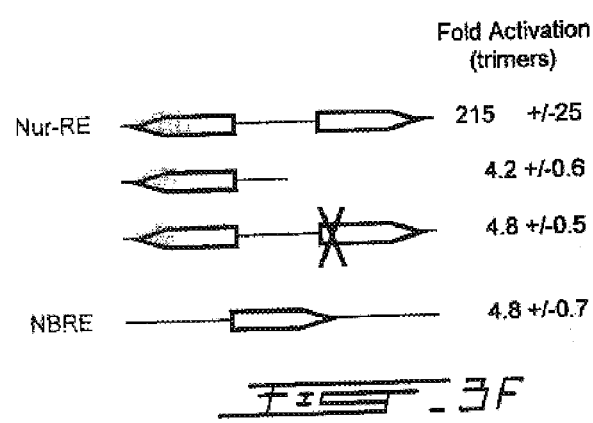

The importance of each motif for binding of Nur77 homodimers was confirmed in gel retardation experiments; indeed, mutation of either motif (mutants M1 and M3) prevented formation of homodimer complexes whereas mutation of intervening sequences (mutant M2) did not (FIG. 3E). The binding of Nur77 monomers to the M1 and M3 mutants is consistent with the observation that the Nur-RE half-sites are similar to NBRE. The Nur-RE is somewhat unusual in sequence in that its two inverted half-sites or NBRE-related motifs are separated by 6 or 10 bp depending on whether one considers the octamer sequence recognized by Nur77 (Wilson et al., 1992, supra) or the hexamer motif used to classify other nuclear receptor target sites (Wilson et al., 1993, supra; Beato, 1989, Cell 56:335–344); thus, in the usual nomenclature (Beato, 1989, supra), the Nur-RE is an ER-10 element. Previous work has shown that DNA recognition by Nur77 (NGFI-B) extends by 2 bp upstream of the canonical hexanucleotide AGGTCA by comparison to other nuclear receptors and that this interaction involves amino acid residues outside of the zinc finger domain (Wilson et al., 1992, supra). These two A residues are present in each half-site of the Nur-RE (FIG. 3D) suggesting that this mode of DNA recognition is used as it is for Nur77 monomer interaction with NBRE. Replacement of the first A by G in one motif sufficed to abolish Nur-RE activity in response to Nur77 overexpression, as did the deletion of an octamer motif (FIG. 3F). The activity of those Nur-RE mutants is the same as that of the NBRE reporter: it is not clear whether this activity is due to the action of three Nur77 monomers or to weakly binding dimers. However, in the context of the POMC promoter, a single NBRE sequence is totally unresponsive to CRH or Nur77 overexpression while a single Nur-RE appeared sufficient for responsiveness (FIG. 1B and C).

The identification of the Nur-RE as a target for binding of Nur77 dimers raises the question of the biological relevance of the NBRE since this target sequence was originally identified in yeast (Fahmer et al., 1991, supra). Later, NBREs were identified by homology in putative Nur77 target genes, in particular, in genes encoding adrenal steroidogenic enzymes (Mangelsdor et al., 1995, supra), but formal proof that these sequences confer biological response other than in transfection experiments is lacking. Despite its importance in TCR-induced apoptosis (Liu et al., 1994, supra; Woronicz et al., 1994, supra; Calnan et al., 1995, supra), there are as yet no known downstream genes of the Nur77 pathway in T cells. The identification of a potent naturally occurring Nur-RE should facilitate the search for Nur77 target genes which lie downstream of Nur77 in the signaling cascade leading to T cell apoptosis.

The POMC promoter has two potential targets for Nur77: the Nur-RE and the NBRE which is contained within the nGRE (Therrien et al., 1991, supra). The latter binds Nur77 monomers and exhibits a similar activity as NBRE in transactivation experiments (data not shown). Although this putative Nur target site was not found to contribute responsiveness to CRH in AtT-20 cells (FIG. 1B, C), it may play a role under some physiological conditions or in other POMC-expressing cells. This latter possibility is not unlikely since the activity of the upstream Nur-RE is dependent on corticotroph-specific recognition of flanking promoter elements (Therrien et al., 1993, Mol. Cell. Biol. 13:2342–2353). Indeed, the tissue-restricted helix-loop-helx (HLH) factor NeuroD/BETA2, and the bicoid-related factor Ptx1, which are important determinants of corticotroph-specific POMC transcription, bind just downstream of the Nur-RE (Lamonerie et al., 1996, Genes Dev. 10:1284–1295).

Prior work Therrien et al., 1993, Mol. Cell. Biol. 13:2342–2353) clearly suggested that the NurRE would not be active in the absence of these two factors. Thus, modulation of NeuroD1 or Ptx1 activity in POMC-expressing corticotroph cells might alter the responsiveness of the POMC gene to Nur77 and consequently to signals like CRH that control Nur77 expression. In conditions where upstream corticotroph-specific promoter regulatory elements are not active, the NBRE/nGRE might become an active target of Nur77 (Murphy et al., 1997, Mol. Endocrnol. 11:39–47), particularly if other transcription factor(s) acting in the proximity of the NBRE/nGRE enhanced its activity.

The convergence of CRH and cAMP signals at the Nur-RE in the POMC gene may seem surprising. However, the POMC promoter does not contain a CRE element and forskolin did not fully mimic the effect of CRH on Nur-RE reporters (FIG. 2), suggesting that forskolin effects may be indirect. CRH was also shown to elevate intracellular $Ca^{++21}$ and $Ca^{++}$-dependent signals have been implicated in Nur activation in T cells (Woronicz et al., 1995, Mol. Cell. Biol. 15:6364–6376; Yazdanbakhsh et al., 1995, Proc. Natl. Acad. Sci. USA 92:437–441). Thus, it may be that different signals converge on Nur77 to modulate POMC transcription.

It was previously suggested that c-fos might in part mediate the effect of CRH (Boutillier et al., 1995, Mol. Endocrnol. 9:745–755): however, that work was performed with serum-starved cells and deletion of the c-fos target AP1 site of the POMC promoter did not prevent CRH stimulation of POMC transcription [our unpublished observations and (Boutillier et al., 1995, supra)]. Thus, CRH activation of Nur77 might represent the primary pathway of CRH signaling in corticotroph cells; in some conditions, CRH-induced c-fos might also contribute to those signals (Autelitano et al., 1993, Mol. Cell. Endocrinol. 94:111–119; Boutillier et al., 1995, supra).

In conclusion, the Nur77 signaling pathway appears to be an important positive regulator of the hypothalamopituitary-adrenal axis since Nur77 and related factors (Law et al., 1992, Mol. Endocrinol. 6:2129–2135) mediate activation of the axis at all three levels, hypothalamus (CRH), pituitary (POMC), and adrenals (steroidogenic enzyme-coding genes). Since we show below that the positive action of Nur77 is antagonized by glucocorticoids, the Nur77 signaling pathway may be the point of convergence for different regulatory signals in both endocrine and lymphoid systems.

EXAMPLE 9
Antagonisms Between Nur77 and Glucocorticoid Receptor for Control of Transcription The finding of a Nur77 signaling pathway activated in POMC-expressing cells in response to CRH shown above prompted the consideration of its relationship to the mechanisms of Gc repression.

The hypothalamic hormone CRH is a major stimulus of pituitary ACTH secretion and of POMC transcription [Jacobson et al., 1994, Regulation of proopiomelanocortin gene transcription, p. 117–138. In H. Imura (ed.)], The pituitary gland. Raven Press, Ltd. New York). Its actions are antagonized by Gc in a classical negative feedback loop. Indeed, the hypothalamo-pituitary-adrenal axis (HPA) is activated by CRH which, through ACTH, leads to increased production of Gc; these steroids feedback at both hypothalamic and pituitary levels to inhibit hormone secretion and repress gene (CRH and POMC) activity. Thus, the interrelationship of positive signals channeled through CRH, and the negative feedback of Gc at both hypothalamic and pituitary levels is thought to set the activity of the HPA axis. The POMC promoter regulatory target for CRH has been identified (see above) and shown to be a novel binding site for the orphan nuclear receptor, Nur77. The interrelationship of Nur family members, Nur-RE and GC/GR was therefore analyzed.

EXAMPLE 10
Transfections

Transfections in AtT-20 cells were performed by lipofection (Lipofectamine, Gibco) using exponentially growing AtT-20 cells ($7.5 \times 10^5$) in 35 mm Petri dishes. Cells were grown in DMEM with 10% fetal calf serum stripped with dextrancoated charcoal (Drouin et al., 1976, Endocrinology 98:1528–1534). Cells and media were harvested 16 h after lipofection. Each sample for lipofection contained a total of 1.5 µg DNA, including 300 ng reporter plasmid, 300 ng RSV-GH as internal control, 100 ng of pCMX-Nur77 expression vector, and total DNA was completed to 1.5 µg with pSP64. Where indicated, CRH and Dex were added at $10^{-7}$M. The POMC promoter constructs were described previously (Therrien et al., 1991, Mol. Cell. Biol. 11:3492–3503; Therrien et al., 1993, Mol. Cell. Biol. 13:2342–2353). In particular, the NurRE and nGRE linker scanning replacement mutations were described previously as mutants 3 and 15 in a series of promoter mutations (Therrien et al., 1991, supra). DO 11.10 cells ($3.5 \times 10^8$ in 0.35 ml SMEM) were electroporated using a Biorad instruments at 250 V, 960 µFarad, and 10 µq each of reporter plasmid and expression vectors. After electroporation, cells were plated in SMEM containing 5% fetal calf serum with or without $10^{-7}$M Dex, antiCD3 (clone 145-2C11) was used at 1 µg/ml to coat dishes (Iwata et al., 1991, Eur. J. Pharmacol. 21:643–648). TUNEL assay was performed as described (Sgonc et al., 1994, Trends Genet. 10:41–42). CV-1 cells ($5 \times 10^5$ cells/35 mm dish) were grown in charcoal-stripped serum and transfected by the calcium phosphate method using 2 µg/dish of reporter plasmid, 1 µg/dish of the internal control plasmid RSV-GH and the indicated amounts of expression plasmids. Total transfected DNA was kept constant at 5 µg/dish using pSP64. Data are presented as the means ± SEM of 3 to 5 experiments each performed in duplicate.

EXAMPLE 11
Northern Blots

Total RNA (20 µg) extracted from AtT-20 cells was used in Northern blot experiments performed as described previously (Lamonerie et al., 1996, Genes Dev. 10:1284–1295).

EXAMPLE 12
Gel Retardation

NurRE, NBRE and TRE oligonucleotides were 3'-end-labeled using Klenow polymerase and purified on polyacrylamide gels. Binding conditions were as previously described (Drouin et al., 1993, supra; Drouin et al., 1992, Mol. Endocrinol. 6:1299–1309; Yang-Yen et al., 1990, supra). In vitro translated Nur77, GR and c-jun were produced using reticulocy lysate kits purchased from Promega (TNT Sp6/T7). The efficiency of protein synthesis was monitored by $^{35}$S-Met labeling of the reaction products and analysis by gel electrophoresis; similar amounts (about 10 ng) of in vitro synthesized Nur77, GR and c-jun were utilized.

EXAMPLE 13
Localization of Dex Responsive Sequences

Figure 4A:
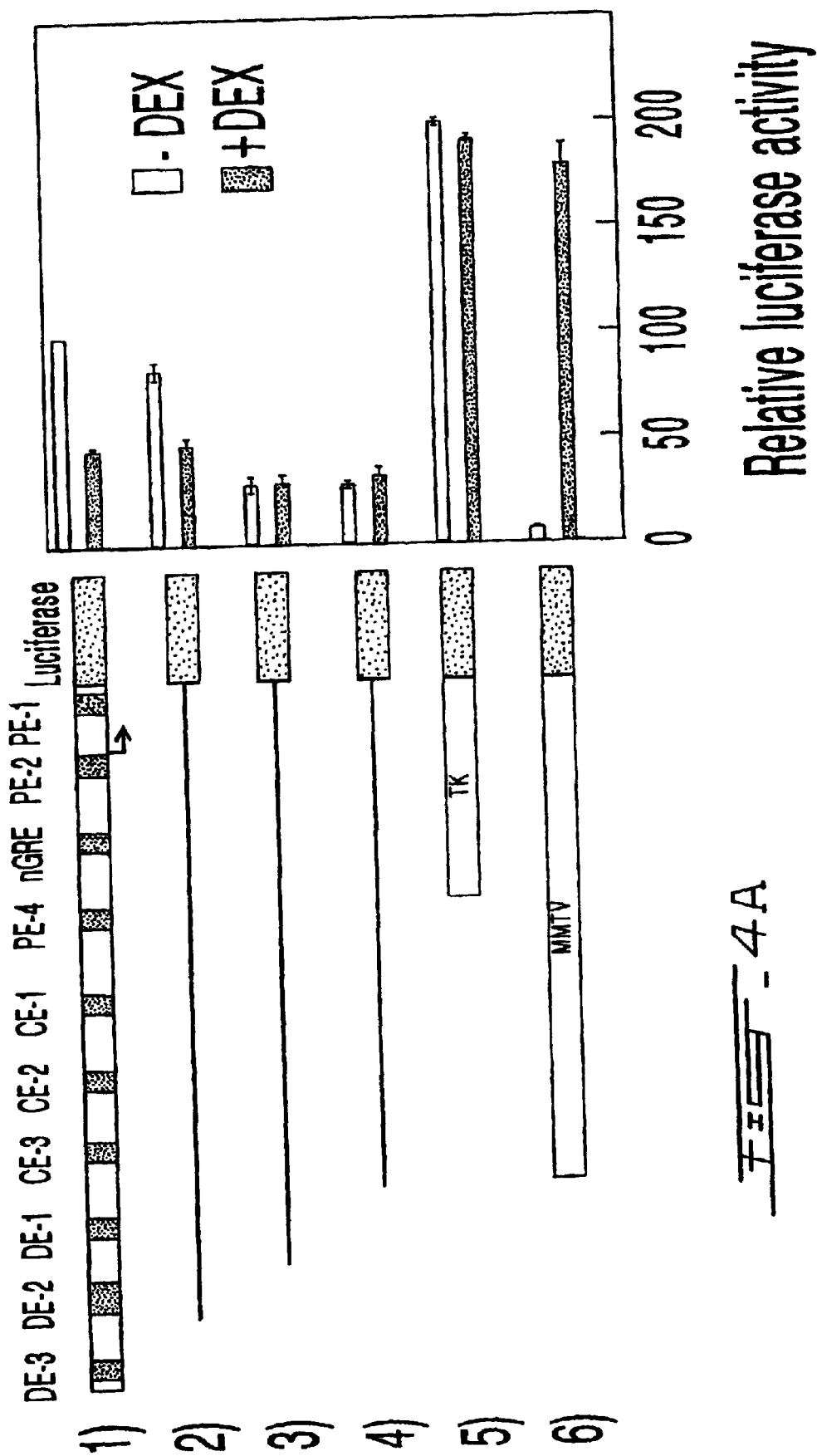
FIG. 4 shows the localization of glucocorticoid target sequences in the POMC promoter. A) Promoter deletions. A rat POMC promoter (−480 to +63 bp)-luciferase reporter was used in transfection experiments in AtT-20 cells and the organization of its regulatory elements is indicated in the diagram for construct 1. The activity of promoter deletions was assessed in the presence and absence of dexamethasone (Dex) $10^{-7}$M and compared to that of TK and MMTV promoters. B) Localization of Dex responsive sequences to the DE2A subelement which overlaps the NurRE. Oligonucleotides were inserted upstream of the central region of the promoter (Therrien et al., 1991, supra; Therrien et al., 1993, supra) in order to localize DE2 sequences implicated in Dex responsiveness. C) The DE2 element confers Dex responsiveness to a minimal promoter construct. Promoter constructs only constituted of oligonucleotides for the Ptx1 target CE3 and for DE2 were used to show dependence on the DE2AB region for Dex sensitivity in the simplest promoter context.
Figure 4B:
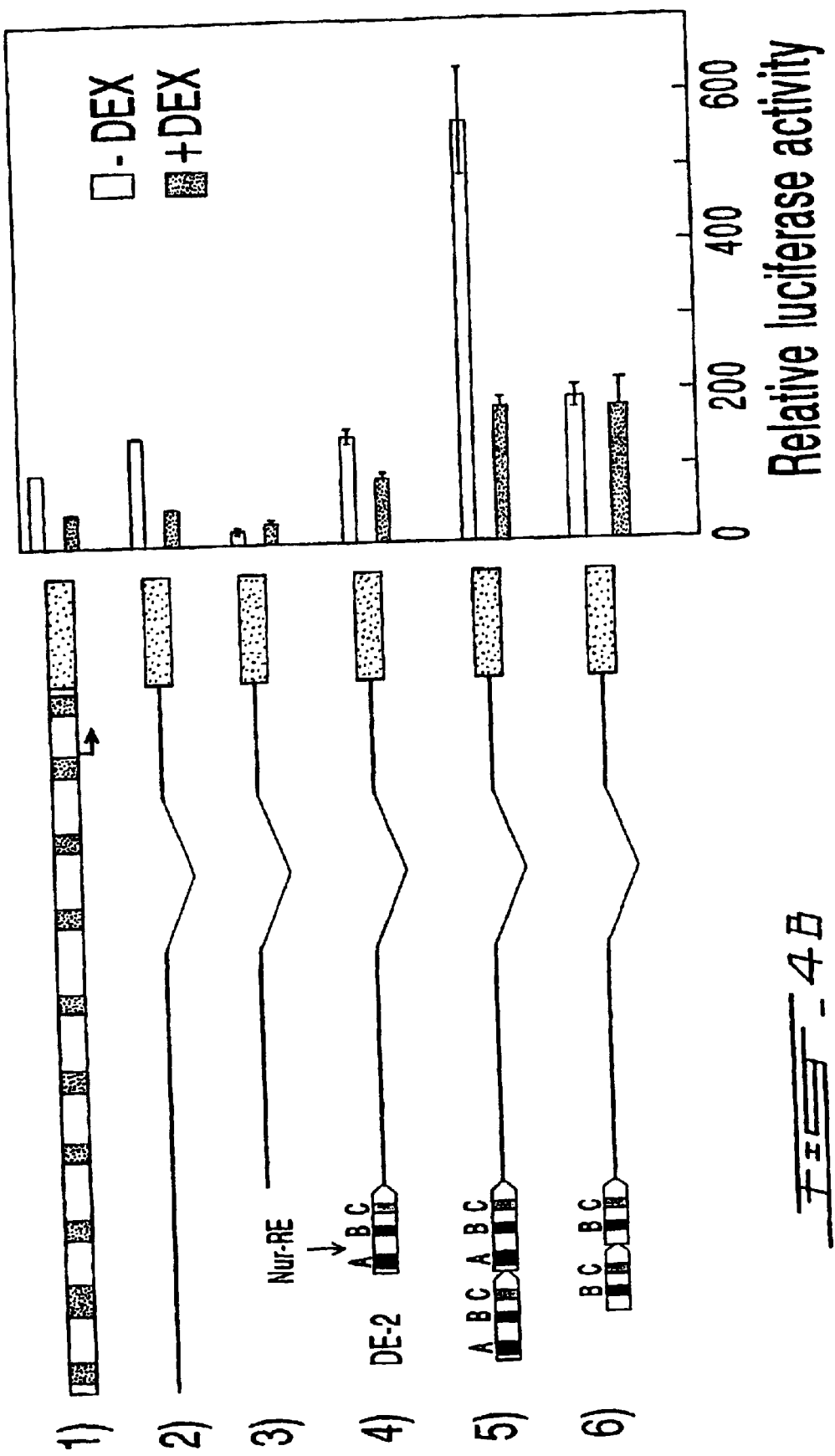
Figure 4C:
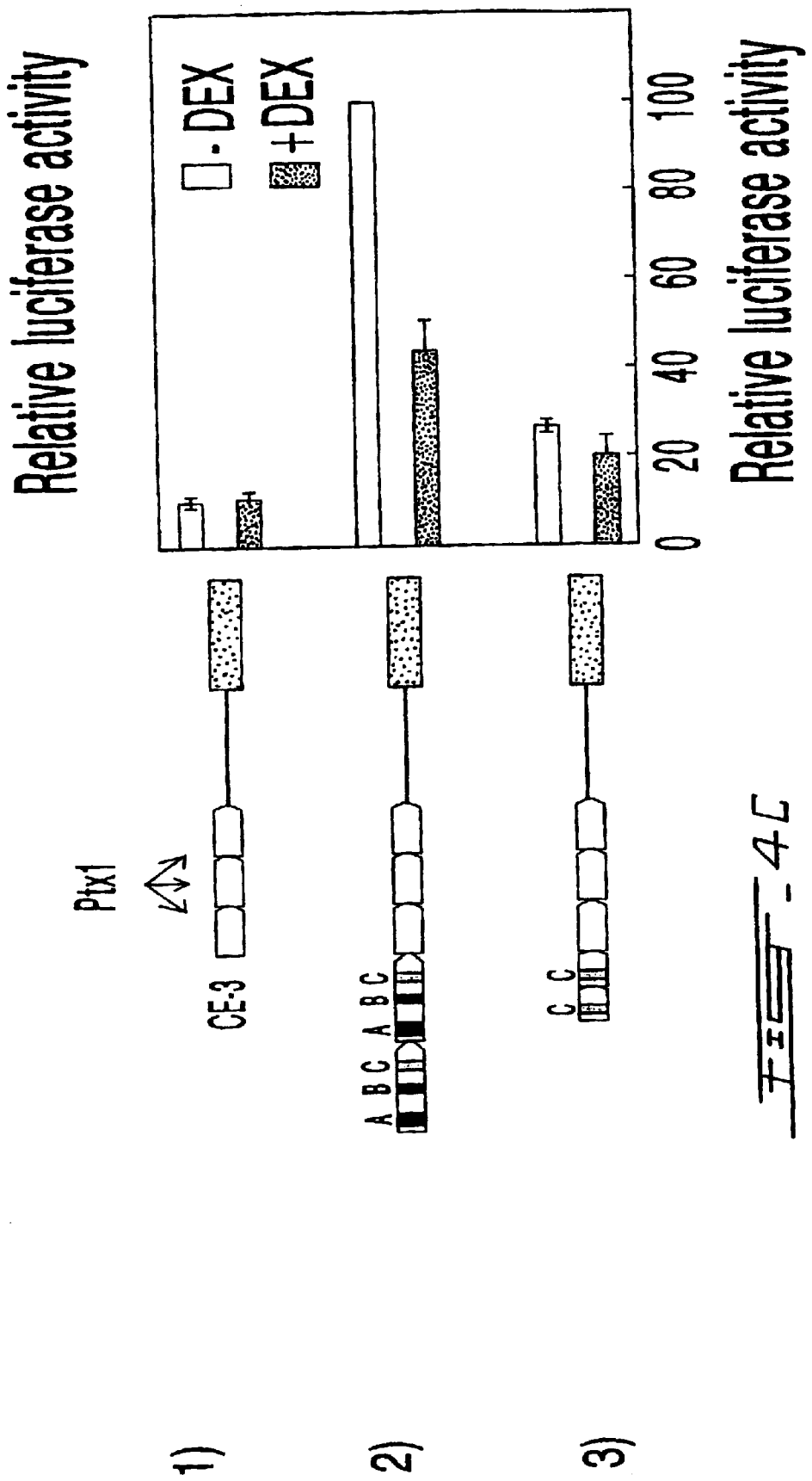
Figure 12:
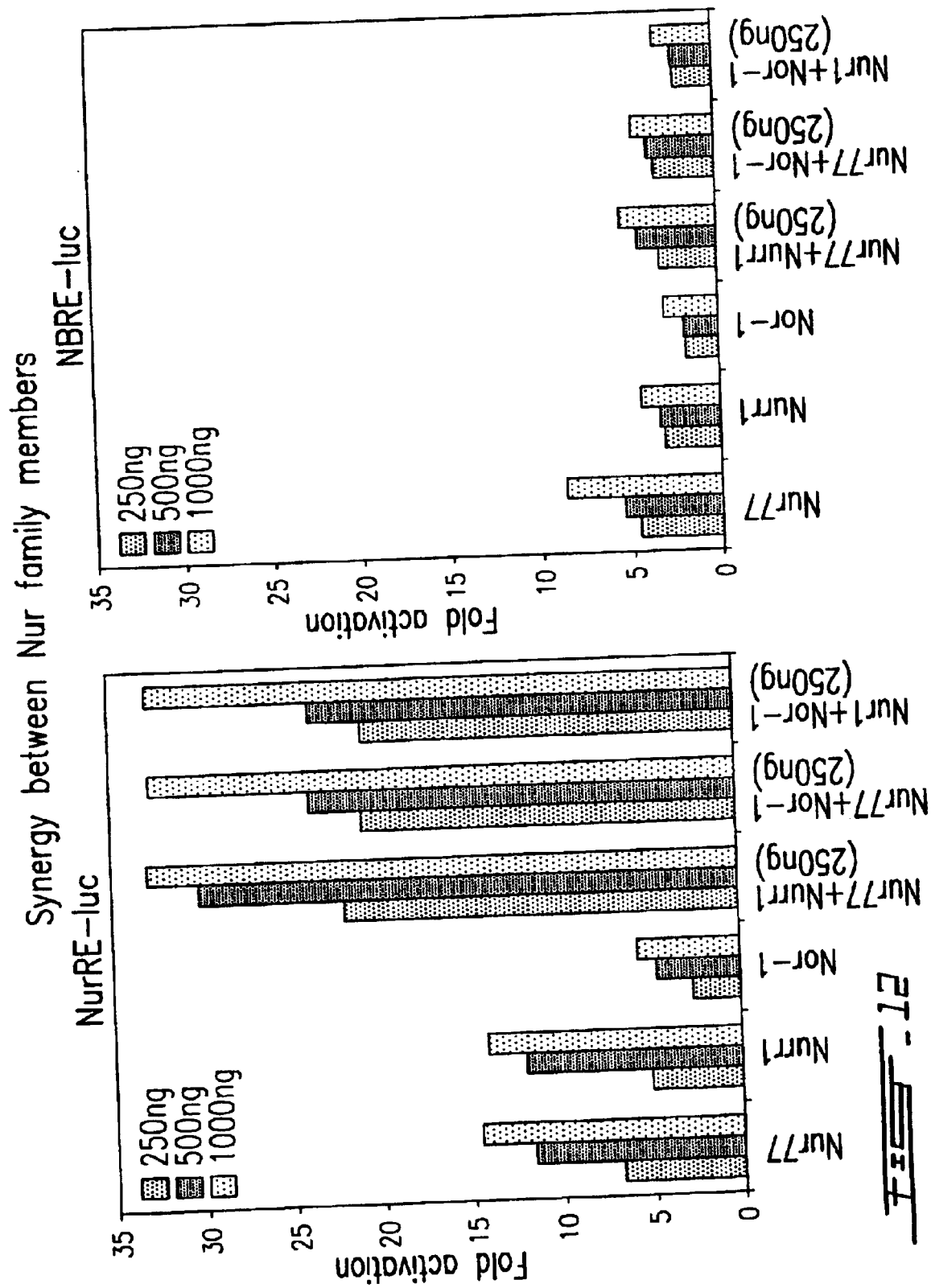
FIG. 12 shows that other Nur family members activate Nur-RE-dependent transcription and shows the synergy between Nur family members at Nur-RE target sites. The effect of the various Nur family transcription factors was tested on Nur-RE and NBRE-containing reporter plasmids. Various amounts of Nur77, Nurr-1 or NOR-1 expression plasmids were transfected in L cells as previously described. In addition, the combination of each pairs of two Nur family members was tested. Luciferase activity was monitored as previously described.

Promoter sequences required for Gc repression of the POMC promoter were localized by lipofection of POMC promoter/luciferase constructs into POMC-expressing AtT-20 cells. This analysis revealed that a composite regulatory element in the distal region (Therrien et al., 1991, supra; Therrien et al., 1993, supra) of the promoter, DE2, is required as its deletion completely blunts responsiveness to the synthetic Gc dexamethasone, Dex (FIG. 4A, compare construct 3 with constructs 1 and 2). The magnitude of the repression (2- to 3-fold) is similar to that observed by nuclear run-on experiments using in vivo (Gagner et al., 1985, Mol. Cell. Endocrinol. 40:25–32) and tissue culture models (Gagner et al., 1987, Mol. Endocrinol. 1:677–682): thus, repression of transfected reporters is very similar to that measured for the POMC gene in normal pituitary cells. In contrast, deletion of the PE-1 regulatory element (Therrien et al., 1991, supra) which contains an AP-1 site (construct 5) does not prevent Gc repression although repression may be of a lesser magnitude. Further, deletion of the proximal region of the promoter that contains a previously described nGRE (Drouin et al., 1993, supra), did not prevent Gc repression either (FIG. 4B construct 2). However, addition of a DE2 oligonucleotide to a basic reporter construct conferred Gc sensitivity (FIG. 4B constructs 3, 4 and 5), and deletion of its upstream region [previously described as DE2A (Therrien et al., 1993, supra)] abolished this response (FIG. 4B, construct 6). Thus, sequences required for responsiveness to Gc lie upstream of those required for synergistic interaction between the bHLH-restricted factor NeuroD1 that binds the DE2C subelement and Ptx1, a bicoid-related homeobox factor, that binds the downstream CE3 element of the promoter (Lamonerie et al., 1996, supra; Poulin et al., 1997, Mol. Cell. Biol. In press; Therrien et al., 1993, supra). The strict dependence on those upstream DE2 sequences was shown using promoter constructs only constituted of oligonucleotides (FIG. 4C). These contained the targets for Ptx1 and the bHLH NeuroD1/BETA2 heterodimers (Lamonerie et al., 1996, supra; Poulin et al., supra). This construct (FIG. 4C, construct 2) exhibited cell specificity (Lamonerie et al., 1996, supra), responsiveness to CRH and Nur77 and it was sensitive to Gc (FIG. 4C). Deletion of all (FIG. 4C, construct 3) or part (FIG. 4B, construct 6) of the NurRE element (that overlaps the A and B boxes of DE2) abolished Gc sensitivity. Thus, the NurRE appears to be a target of Gc action in addition to conferring responsiveness to Nur77 and CRH. This demonstrates that glucocorticoids reverse the Nur-RE-dependent Nur77 transcriptional activation. Moreover, this reversion of Nur77 Is also manifested phenotypically as TCR-induced apoptosis is reversed by the addition of glucooiticolds (data not shown).

EXAMPLE 14
The NurRE Confers Responsiveness to Dex

In order to test whether Nur-RE confers responsiveness to Dex, we determined whether the activation of POMC transcription by CRH (FIG. 5A) and Nur77 (FIG. 5B) was antagonized by Dex. Indeed, in addition to repressing basal POMC promoter activity, Dex also reversed the activation by CRH and Nur77 overexpression (FIG. 5 construct 1). Whereas mutagenesis of the nGRE (construct 2) had no effect on either response, mutagenesis of the NurRE (by transversion of 10 bp, construct 3) decreased promoter activity to that of the Dex-repressed intact promoter and completely blunted Dex repression in basal and CRH or Nur77-stimulated conditions. In our experimental conditions, the −323 bp promoter (construct 4) that contains both nGRE (which itself contains a NBRE target for Nur77) and an AP-1 site did not respond to CRH, Nur77 or Dex; similarly, the minimal promoter (construct 5) that still contains the AP-1 site in its exonic portion did not respond. The NurRE thus seems to be the point of convergence for both positive (CRH and Nur77) and negative (Gc) signals controlling POMC transcription.

The convergence of CRH, Nur77 and Gc signals at the NurRE was clearly shown using a reporter that contained only that regulatory element in three copies (FIG. 6A and B). Indeed, the large activity elicited by CRH stimulation using the NurRE-luc reporter was completely reversed by Dex (FIG. 6A), and even the supra-physiological induction produced by overexpression of Nur77 was partly reversed by Dex (FIG. 6B). In similar experiments, overexpression of GR led to a greater Dex-dependent reversal of Nur77 activation (data not shown). Antagonism between Nur77 and Dex was also observed with a NBRE-luc reporter although the magnitude of the effects was significantly smaller (data not shown, about 40 fold less).

EXAMPLE 5
Dex Antagonism is Partly Exerted on Nur77 Expression

Although the Gc reversal of Nur77dependent reporter activity suggested an interaction at the transcriptional level, we tested whether these signals may not also converge at the Nur77 gene Itself as it is very strongly induced in response to CRH. Northern blot analysis of AtT-20 cells treated with CRH and/or Dex indicated that Dex reduced the CRH induction of Nur77 mRNA but only by about 50% (FIG. 7). Thus, it appears that Gc blunt the Nur77 signaling pathway at two levels, namely induction of Nur77 transcription (FIG. 7) and the transcriptional effect of Nur77 itself on its target (FIG. 6).

EXAMPLE 16
Reciprocal Titration of Nur77 and GR Action

The transcriptional interaction between Nur77 and GR could take place at different levels during activation of transcription. It has been previously shown that GR does not bind the NurRE (Drouin et al., 1989, Mol. Cell. Biol. 9:5305–5314), suggesting that protein:protein interactions are involved in the antagonism between GR and Nur77. In order to test whether the antagonism between GR and Nur77 is reciprocal, we expressed in CV-1 cells increasing amounts of GR in presence of Nur77 and NurRE-luc reporter, and vice versa with a GRE-containing reporter (FIG. 8). Both GR and Nur77 titrated each other's activity on its cognate reporter. Thus, increasing concentrations of GR blunted the Nur77 activation at the NurRE only in presence of Dex (FIG. 8A) and Dex had no effect in the absence of GR (ratio 1/0). Conversely, the Dex-dependent transactivation by GR was reversed in a dose-dependent manner by Nur77 (FIG. 8B). Dex did not activate this reporter In the absence of GR expression (data not shown). These data suggest that the two factors antagonize each other by direct interaction between them or by interaction with a common target.

To assess a putative interaction between Nur77 and GR, we tested the effect of one factor on the DNA binding activity of the other (FIG. 9). The antagonism between GR and AP-1 was reflected in vitro by an impairment of the DNA binding of each factor to its cognate element (Kerppola et al., 1993, Mol. Cell. Biol. 13:3782–3791; Schüle et al., 1990, supra; Yang-Yen et al., 1990, supra). The in vivo significance of this interaction has been questioned (Konig et al., 1992, EMBO J. 11:2241–2246) but the current models of integration of transcription factor signals by CBP/p300 are consistent with interactions between the factors as well as with CBP/p300 (Kamei et al., 1996, Cell 85:403–414). Similarly, we found that the binding of in vitro translated Nur77 to a NurRE probe was impaired in presence of GR (FIG. 9, lanes 4 to 7) but not with similar amounts of in vitro translated c-jun (lanes 8 to 10). Conversely, addition of Nur77 in GR binding assays to a GRE probe led to a significant decrease of GR binding (lanes 14 to 17). Interestingly, similar amounts of c-jun did not impair GR binding (lanes 18 to 20). Higher amounts of c-jun were required to do so (data not shown) in agreement with previous work (Yang-Yen et al., 1990, supra) and with data indicating that c-jun is less potent than c-fos for inhibition of in vitro GR binding (Kerppola et al., 1993, supra). The c-jun preparation used in these experiments was active in TRE binding (lane 24). Thus, the GR-Nur77 interaction appears to occur at protein concentrations that are similar or lower than those involved in GR/AP-1 interactions.

EXAMPLE 17
GR Domains Required for Repression of Nur77 Action

Figure 10:
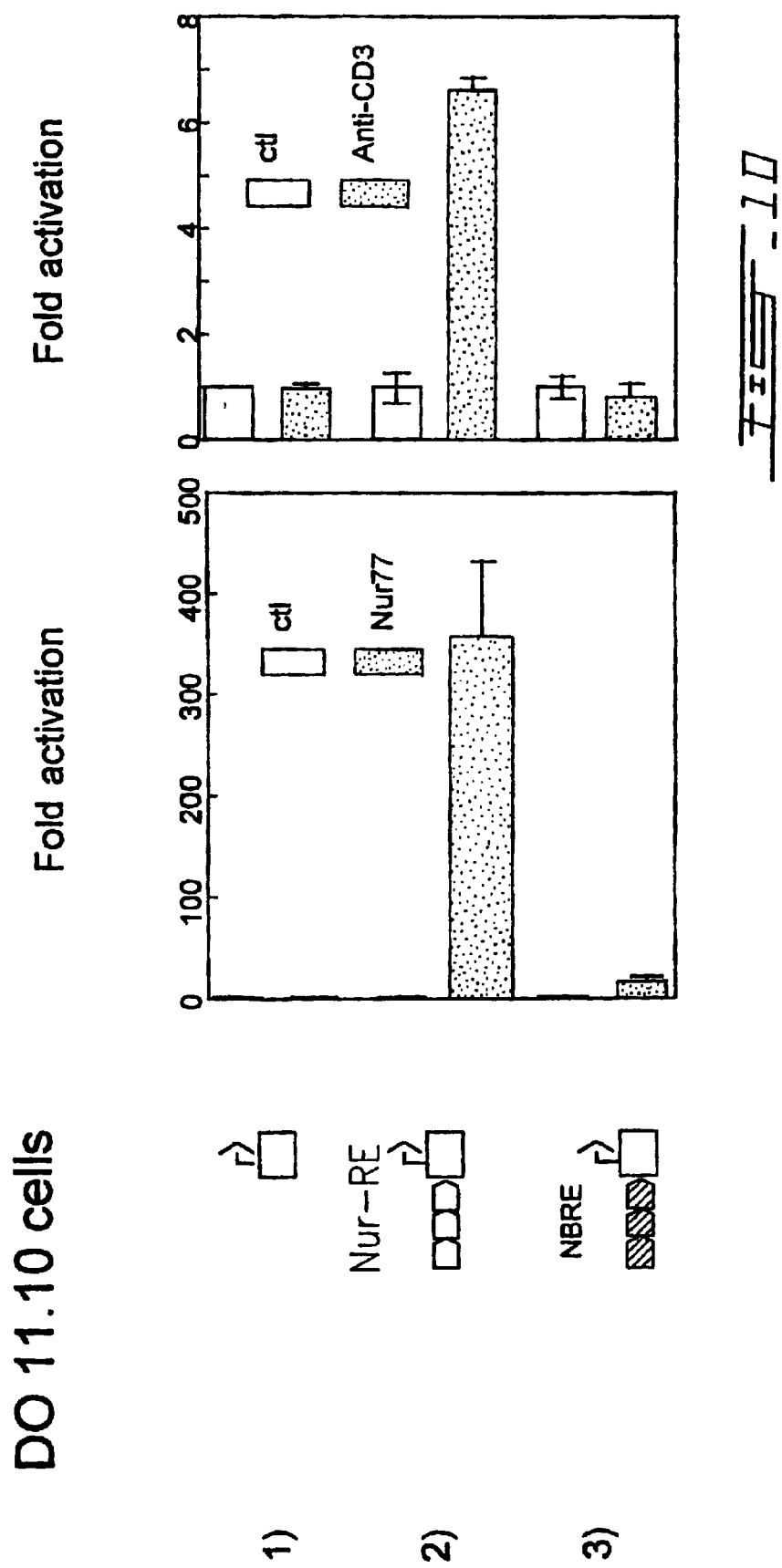
FIG. 10 shows the localization of GR domains required for repression of Nur77dependent activation of NurRE-luc reporter. A set of previously described GR mutants (schematically represented on right) was used in co-transfection experiments in CV-1 cells with the NurRE and GRE reporters described in the legend to FIG. 8. For the GRE reporter, activity is only shown in presence of Dex as it was extremely low in its absence, except for mutant VAN 525 which has constitutive Dex-independent activity (Yang-Yen et al., 1990, supra). The expression vectors for GR mutants were used at 500 ng/dish.

The domains of GR required for repression of Nur77 action at NurRE were localized using a panel of GR mutants that were previously assessed for their effect on Gc-dependent activation of transcription and for repression of AP-1-induced transcription (Helmberg et al., 1995, EMBO J. 14:452–460; Jonat et al., 1990, supra: Schüle et al., supra; Yang-Yen et al., 1990, supra). Each GR mutant was tested for its capacity to activate transcription from a GRE containing reporter in the presence or absence of Dex, as well as for its capacity to repress Nur77induced transcription of the NurRE reporter (FIG. 10). Deletions of the N terminal transactivation domain of GR did not interfere with Dex-dependent repression whereas most mutations in the DNA binding domain that prevented DNA binding as well as Gc-dependent induction of transcription, also prevented repression of Nur77-dependent activity. Interestingly, the LS7 mutant that was previously shown (Godowski et al., 1987, Nature 325:365–368; Helmberg et al., 1995, supra; Yang-Yen et al., 1990, supra) to be deficient in activation function but still active in repression of AP-1-dependent transcription, is also active in repression of Nur77-dependent activity. Deletion of the ligand binding domain produced a receptor (mutant VAN525) that represses Nur77-dependent reporter activity in a hormone-independent fashion; the transactivation activity of this mutant GR is also hormone-independent. Since neither N nor C terminal domains of GR appear to be required for the repression function and since many DNA binding domain (DBD) mutations block repression activity, it appears that this function can be mostly ascribed to the DBD. However, the transactivation and repressor activities of DBD appear separate as evidenced by the LS7 mutant. These findings are strictly similar to those made for GR domains required for repression of AP-1 activity (Heck et at., 1994, EMBO J. 13:4087–4095; Schüle et al., 1990, supra; Yang-Yen et al., 1990, supra) and they suggest that similar GR domains are involved in cross-talk with Nur77 and AP-1.

EXAMPLE 18
Antagonism Between TCR Signaling and Gc at the NurRE

Nur77 appears to be an essential mediator of T cell apoptosis (Calnan et al., 1995, Immunity 3:273–282; Cheng et al., 1997, EMBO J. 16:1865–1875; Liu et al., 1994, Nature 367:281–284; Woronicz et al., 1994, Nature 367:277–281). Since the apoptotic response of T cells to TCR activation is antagonized by Gc (Iwata et al., 1991, supra; King et al., 1995, Immunity 3:647–656), we tested whether Dex antagonizes NurRE-luc reporter activity induced by TCR activation produced by cross-linking with an antiCD3 antibody (FIG. 11). The DO11.10 T hybridoma cells used in these experiments are induced into apoptosis by antiCD3 treatment and by Gc through independent pathways; however, the two antagonize each other (Iwata et al., 1991, supra; King et al., 1994, Int. Arch. All. Immunol. 105:355–358). Preliminary experiments using the TUNEL assay (Sgonc et al., 1994, supra) to identify apoptotic cells were conducted in order to determine optimal concentrations of anbCD3 and Dex for assessment of NurRE reporter (FIG. 41A). In contrast to AtT-20 cells where basal NurRE-luc reporter activity is very low and insensitive to Dex treatment (FIG. 6), Dex decreased basal reporter activity In DO11.10 cells by almost as much as it repressed the antiCD3-induced activity (FIG. 41 B). This is suggestive of a higher endogenous Nur activity in the hybridoma cell line, and may account for the lesser sensitivity to repression by Gc after antiCD3 treatment. Part of this basal activity might have been induced by the electroporation itself. Be that as it may, Gc and Nur77 signaling antagonize each other in T cells as in endocrine cells.

EXAMPLE 9
GC/GR Represses the Signals Mediated Through Nur77 by at Least Two Mechanisms Whereas previous work has suggested that the GR represses transcription of target genes either through direct GR interaction with DNA or through protein:protein interaction with other classes of transcription factors (Drouin, J. 1993, Repression of transcription by nuclear receptors, p. 118–140. In M. G. Parker (ed.), Frontiers in molecular biology: Steroid hormone action. Oxford University Press, England), the present data suggest that GR-mediated repression may also result from antagonism with other members of the nuclear receptor family. Indeed, Nur77 is a member of a small subfamily of orphan nuclear receptors that appear to play important signaling functions in the HPA axis (Davis et al., 1994, Mol. Cell. Biol. 14:3469–3483: Honkaniemi et al., 1994, Brain Res. 25:234–241; Murphy et al., 1997, Mol. Endocrinol. 11:39–47; Parkes et al., 1993, Mol. Endocrinol. 7:1357–1367) and in T cells (Calnan et al., 1995, supra; Egan et al., 1995, Dev. Biol. 170:397–419; Liu et al., 1994, supra; Woronicz etal., supra). At this time, it is not clear whether Nur77 requires ligand activation as no ligand is known for this factor and as it is obviously active in transcription activation experiments without addition of any exogenous ligand. The present work supports at least two mechanisms for Gc/GR repression of signals mediated through Nur77. Indeed, we have shown that Gc blunt the responsiveness of the Nur77 gene to a physiological signal, CRH (FIG. 7) and we have shown that GR antagonizes Nur77-dependent activation of transcription in three different systems (FIG. 6, 5 and 8). The mechanism of this antagonism appears to be similar to that for cross-talk between GR and AP-1. The implication of GC/GR repression concerning on Nur family members opens the way to the dissection of the molecular determinants of this repression. In view of the importance of GC/GR in cells physiology and homeostasis, the present invention has major research, industrial, and therapeutic applications.

EXAMPLE 20
Repression of POMC Transcription by GR

Repression of POMC expression by Gc is an important regulatory component of the HPA axis, and disregulation of this negative feedback loop has physiological and behavioral consequences as exemplified in Cushing's disease or in patient or animals with chronic stress. In vivo studies both in humans and animal models, have indicated that the sensitivity of the HPA axes to Gc can vary enormously depending of physiological status. The molecular basis for this modulation is sell poorly understood. The POMC gene has offered a model gene to define the mechanisms of Gc repression and potentially to define mechanisms involved in modulation of Gc responsiveness in the HPA axis. Previous studies have implicated up to three targets of the POMC promoter in Gc repression. They include the nGRE located in the proximal region of the promoter and shown to form unique complexes with three molecules of GR (Drouin et al., 1993, supra; Drouin et al., 1989, supra). Other studies have implicated the nGRE together with upstream promoter targets in Gc repression (Riegel et al., 1991, supra). Finally, it has been suggested that a fos-dependent mechanism may be involved in some conditions (Boutillier et al., 1995, supra); fos and related members of the AP-1 family of transcription factors exert their transcriptional effect on POMC transcription through a binding site in the first exon of the gene [element PE1 of the promoter, (Therrien et al., 1991, supra)]. The present work has defined the upstream promoter target for Gc repression as the NurRE (FIG. 4, 2 and 3). At this time, it is not clear what mechanism may control the contribution of each of these promoter targets to Gc repression. However, the fos-mediated pathway may operate in unusual conditions as it was entirely defined in serum-starved cells and deletion of the POMC promoter AP-1 target site (FIG. 4A, construct 5) does not after Dex repression significantly. Whatever the role of AP-1 in POMC expression, it is clear that it is not sufficient to mediate Gc repression. The NurRE pathway may be dependent on corticotroph-specific recognition of the promoter which requires NeuroD heterodimers acting at the DE2C subelement and Pbx1 acting on the CE3 element (Lamonerie et al., 1996, supra; Therrien et al., 1993, supra).

Indeed, our original promoter analyses had indicated that the DE2-AB sub-element which includes the NurRE is mostly active when of the DE2C/CE3 elements are active in synergism (Therrien et al., 1991, supra; Therrien et al., 1993, supra). Thus, in non-corticotroph cells or in corticotroph cells in which the activity of Ptx1, NeuroD or its dimerization partner is reduced through signaling events, the NurRE target may be inoperative. This could be a mechanism through which desensitization of corticotroph cells to Gc repression might be achieved in conditions such as chronic stress.

The nGRE is a potential target for both GR and Nur77 as it contains a NBRE sequence (Murphy et al., 1997, supra; Wilson et al., 1991, Science 252:1296–1300). In the experimental conditions of the present study in AtT-20 cells, POMC promoter activity was very dependent on upstream cell-specific sequences (FIG. 5) and in these conditions, the nGRE/NBRE was not responsive to either Nur77 overexpression, CRH or to Gc repression (FIG. 5). In other conditions, the nGRE was shown to contribute as a target for Gc repression (Drouin et al., 1993, supra; Drouin et al., 1989, supra; Murphy et al., 1997, supra; Riegel et al., 1991, supra) and, in isolation on a minimal promoter (FIG. 6), a NBRE reporter was responsive to Nur77 overexpression as well as to Dex, albeit at much reduced magnitude compared to the NurRE. In these latter cases (where the distal promoter sequences may have been inoperative), two mechanisms might have involved Nur77. First, protein:protein interactions of the same nature as those involved in GR antagonism at the NurRE could be implicated (discussed below). Second, mutually exclusive binding of GR and Nur77 at the nGRE is also possible. Irrespective of the mechanism, such antagonism could only be operative in conditions where a positive transactivator like Nur77 activated transcription through interaction with nGRE/NBRE. Consequently, the nGRE would not be expected to behave as a target for Gc repression in basal conditions, as prior work showed that mutagenesis of nGRE sequences did not affect basal POMC promoter activity in AtT-20 cells (Therrien et al., 1991, supra). In contrast, since Gc do repress basal POMC transcription in AtT-20 cells (Drouin et al., 1993, supra; Drouin et al., 1989, supra; Eberwine et al., 1984, J. Biol. Chem. 259:2166–2170; Gagner et al., 1987, supra) and in primary cultures of pituitary cells (Gagner et al., 1987, supra), the primary target for Gc repression is most likely to be the NurRE which is tightly linked to cell,specific recognition of the promoter in corticotroph cells. However, in some conditions, like in chronic stress, the relative contribution of proximal promoter sequences (which include the nGRE) to basal control of transcription might be enhanced (by a mechanism yet to be identified) and thus, the nGRE become an effective target for Gc repression.

EXAMPLE 21
Mechanism of GR/Nur77 Antagonism

The present data suggest that GR repression of Nur77-dependent transcription is mediated by protein:protein interactions either between these two proteins (FIG. 9) or between these two and a common target. Such common target could be one of the many co-activators or co-repressors that have been associated with the transcriptional activity of nuclear receptors (Horlein et al., 1995, Nature 377:397–404; Onate et al., 1995, Science 270:1354–1357). In particular, CBP/p300 has been implicated in mediating the transcriptional effects of nuclear receptors and also of the jun/AP-1 family of factors (Kamei et al., 1996, supra). As Nur77 and GR are both of the same structural family of nuclear receptors, it will be interesting to determine whether they both interact with CBP at the N-terminus as shown for GR (Kamei et al., 1996, supra) or whether they interact at different sites on CBP.

A parallel can be drawn between the present data (FIG. 8, 6 and 7) and the antagonism between GR and AP-1 (Jonat et al., 1990, supra: Kerppola et al., 1993, supra; Schüle et al., 1990, supra; Yang-Yen et al., 1990, supra), and possibly also with relA/NFkB-induced transcription (Auphan et al., 1995, Science 270:286–290; Caldenhoven et al., 1995, Mol. Endocrinol. 9:401–412; Scheinman et al., 1995, Science 270:283–286; Scheinman et al., Mo. Cell. Biol. 15:943–953). Indeed, in these cases, GR-mediated repression is ligand-dependent and does not require DNA binding although the DBD is involved. The mechanism of this ligand-dependent repression is presumably different from that recently described for unliganded receptors which involve the hinge regions of TR and RAR (Heinzel et al., 1997, Nature 387:43–48: Horlein et al., 1995, supra; Nagy et al., 1997, Cell 89:373–380). As GR is not known to repress transcription in its unliganded state and as this hinge region is different in GR, another mechanism of repression is likely. Although it is possible that repression and activation might proceed through different intermediate complexes containing either histone deacetylase or acetyltransferase (Wolffe, A. P., 1997, Nature 387:16–17), another possibility might be that the activator effect of Nur77 and the repressor activity of GR are both integrated at the level of CBP. In this case, it would be mom likely that the two factors interact with different sites on CBP rather than compete for the N-terminus (Kamei et al., 1996, supra). This is supported by the fact that the DBD of GR appears to play the primary role in the repressor function whereas the C-terminus of GR and other nuclear receptors was involved in interaction with the CBP N-terminus in a ligand-dependent fashion (Kamei et al., 1996, supra). This may be interpreted to suggest that the receptor C-terminus/CBP N-terminus interaction mediates activator function and that when the same receptors act as DNA-independent repressors, they target another domain of CBP either directly and/or by association with a co-repressor protein. In this model, DNA binding by the nuclear receptor will determine whether it behaves as activator or repressor of transcription. The POMC nGRE night be an exception to this since the three GR molecules bound to this element are unable to activate transcription (Drouin et al., 1993, supra): the unique conformation of GR bound to this element might maintain it in a repressor status despite its interaction with DNA.

EXAMPLE 22
Nur Family Members in General Activate Transcription Through Nur-RE and Evidence of a Synergistic Effect Thereof at Nur-RE In order to validate the activation potential of other Nur family members, the effect of various Nur transcription factors were tested on Nur-RE and NBRE-containing reporter plasmids. Each reporter plasmid contained only one copy of either Nur-RE (Nur-RE-luc) or NBRE (NBRE-luc). Expression plasmids for Nur77, Nurr-1 or NOR1 were constructed using a RSV-LTR promoter to ensure high level expression. Various amounts of these expression plasmids were used in transfection experiments in L cells as indicated. The activity of the Nur-RE-luc reporter was stimulated at all expression vector dosages by overexpression of all three Nur family members, and in each case, this activation was stronger than for NBRE-luc. In addition, the combination of each pairs of two Nur family members exhibited greater activity on the Nur-RE reporter than either Nur family members on its own. Thus, Nur family transcription factors synergically enhance transcription from the Nur-RE but not from the NBRE. This synergism strongly suggests that Nur family members can act as heterodimers on the Nur-RE.

Based on these results, it is foreseeable that a combination of three Nur family members might show a different pattern of modulation of transcription at Nur-RE. The action of GR through Nur-RE further increases the combinations which can be tested in accordance with teachings of the present invention. The herein identified synergy provides a further level of complexity to the transactivation system described, the level of transactivation at Nur-RE appears dependent on the nucleic acid sequence of the target Nur-RE as well as on the protein:protein interaction which occurs there at. The present invention provides the means to dissect these molecular interactions. The present invention further provides numerous means to identify modulators of these molecular interactions. A non-limiting contribution of the present invention is the enablement of the use of Nur-RE in an assay or method to assess and dissect GC/GR antagonism of transcription.

Of importance, the Nur-RE-luciferase constructs used in the present invention contained a single copy of Nur-RE (or NBRE), thus validating the ER-10 structure of the target region as the functional target sequence.

EXAMPLE 23
The Perfect Nur-RE Palindrome

The POMC Nur-RE is constituted of an imperfect palindrome containing two motifs related to the octamer AAAG-GTCA (SEQ ID NO:1) in which each half site matches this consensus motif in six of eight positions. When a perfect palindromic Nur-RE sequence was synthesized (sequence: TGA CC TTT ATT CTC AAAGG TCA) (SEQ ID NO: 33), this perfect consensus Nur-RE palindrome was found to bind Nurr1 and NOR1 with greater affinity than the Nur-RE initially identified in the POMC gene (data not shown).

This perfect palindrome could thus be used, for example, for the construction of expression vectors as well as for assays for the screening of modulators of Nur-dependent transcriptional activation.

Although the present invention has been described hereinabove by way of preferred embodiments thereof, it can be modified, without departing from the spirit and nature of the subject invention as defined in the appended claims.

What is claimed is:

1. An isolated oligonucleotide sequence comprising a response element that binds to a nuclear receptor of the Nur family of nuclear receptors, said response element comprising nucleotide sequence $X_8 L_6 Y_8$, wherein:

a) $X_8$ and $Y_8$ are two half site sequences of 8 nucleotides which are configured as an exerted repeat;

b) $L_6$ separates said half site sequences, with L being 6 nucleotides and being independently selected from A,T,C,or G;

c) $X_8$ having nucleotide sequence $N_6TT$, and $Y_8$ having nucleotide sequence $AAN_6$, wherein N is selected from A,T,C,or G, such that said sequence of $X_8$ and $Y_8$ share homology with the NBRE sequence defined by the hexanucleotide sequence AGGTCA (SEQ ID NO: 3) and its complement TGACCT (SEQ ID NO: 29), respectively, and wherein said response element is capable of binding to a dimer consisting of two partners which are selected from members of the Nur family of nuclear receptors.

2. The oligonucleotide sequence of claim 1, wherein 4 out of 6 nucleotides of $N_6$ are identical to said AGGTCA (SEQ ID NO: 3) or TGACCT (SEQ ID NO: 29) sequences.

3. The oligonucleotide sequence of claim 2, wherein $AAN_6$ has a sequence selected from the group consisting of AAATATCA (SEQ ID NO:7), AAATGCCA (SEQ ID NO:8), AAAGGTCA (SEQ ID NO:1), and functional derivatives thereof.

4. The oligonucleotide sequence of claim 2, wherein $N_6TT$ has a sequence selected from the group consisting of TGATATTT (SEQ ID NO: 30), TGGCATTT (SEQ ID NO: 31), TGACCTTT (SEQ ID NO: 32), and functional derivatives thereof.

5. The oligonucleotide sequence of claim 4, wherein said response element comprises a nucleotide sequence selected from the group consisting of: GTGATATTTXXXXXX-AAATGCCAG (SEQ ID NO:9), TGATATTTXXXXXX-AAATGCCA (SEQ ID NO:10), GTGATATTTXXXXXX-AAATATCAC (SEQ ID NO:11), TGATATTTXXXXXXAAATATCA (SEQ ID NO:12), CTGGCATTTXXXXXXAAATGCCAG (SEQ ID NO:13), TGGCATTTXXXXXX AAATGCCA (SEQ ID NO:14), QTGACCTTTXXXXXXAAAGGTCAQ (SEQ ID NO:1 5), TGACCTTTXXXXXX AAAGGTCA (SEQ ID NO:16), QTGUYATTTXXXXXXAAATUYCAQ (SEQ ID NO:17), TGUYATTTXXXXXXAAATUYCA (SEQ ID NO:18), GTGATATTTACCTCCAAATGCCAG (SEQ ID NO:19), TGATATTTACCTCCAAA TGCCA (SEQ ID NO:20), GTGATATTTACCTCCAAATATCAC (SEQ ID NO:21), TGATATTTACCTCCAAATATCA (SEQ ID NO:22), CTGGCATTTACCTCCAAATGCCAG (SEQ ID NO:23), TGGCATTTACCTCCAAA TGCCA (SEQ ID NO:24), QTGACCTTTACCTCCAAAGGTCAQ (SEQ ID NO:25), TGACCTTTACCTCCAAA GGTCA (SEQ ID NO:26), QTGUYATTTACCTCCAAATUYCAQ (SEQ ID NO:27), TGUYATTTACCTCCAAATUYCA (SEQ ID NO:28), complements and functional derivatives thereof, wherein X is independently selected from A,T,C,or G, U is a purine, Y is a pyrimidine, and Q is C or G.

6. The oligonucleotide sequence of claim 5, wherein said response element comprises a nucleic acid sequence selected from the group consisting of: GTGATATTTXXXXXX-AAATGCCAG (SEQ ID NO:9) and TGACCTTTXXXXXX AAAGGTCA (SEQ ID NO:16).

7. The oligonucleotide sequence of claim 6, wherein said response element comprises nucleic acid sequence TGATATTTACCTCCAAATGCCA (SEQ ID NO:20).

8. The oligonucleotide sequence of claim 6, wherein said response element comprises nucleic acid sequence GTGATATTTACCTCCAAATGCCAG (SEQ ID NO:19).

9. The oligonucleotide sequence of claim 6, wherein said response element comprises nucleic acid sequence TGACCTTTXXXXXXAAAGGTCA (SEQ ID NO:16).

10. The oligonucleotide sequence of claim 1, wherein said member of the Nur family of nuclear receptors is selected from the group consisting of: Nur77, NGFI-B, N10, NAK1, TR3, Nurr-1, RNR-1, NOT, TINUR, NOR-1 and MINOR.

11. The oligonucleotide sequence of claim 1, wherein said response element binds to dimer formed between a first and a second member of said Nur family of nuclear receptors, and wherein said first and said second members are the same member of the Nur family of nuclear receptors, thereby forming a homodimer.

12. The oligonucleotide sequence of claim 1, wherein said response element binds to a dimer formed between a first and a second member of said Nur family of nuclear receptors and wherein said first and said second members are different members of the Nur family of nuclear receptors, thereby forming a heterodimer.

13. A DNA construct comprising the oligonucleotide sequence of claim 1, operably linked to a promoter, which promoter is operably linked to a heterologous gene, wherein the DNA construct is linked in such a manner that the gene is under the transcriptional control of the oligonucleotide sequence and promoter.

14. The DNA construct of claim 13, wherein said oligonucleotide sequence comprises a multimer of at least one of said response element.

15. The DNA construct of claim 13, wherein the heterologous gene is a reporter gene.

16. A host cell transfected with the DNA construct of claim 13.

17. A method for controlled expression of a heterologous gene of interest comprising culturing a host cell according to claim 16 in the presence of an appropriate regulatory protein.

18. The method according to claim 17, wherein the regulatory protein comprises a member of the Nur family of nuclear receptors.

19. A method for detecting a modulator of transcription at a Nur response element (Nur-RE), wherein said Nur-RE is an oligonucleotide sequence comprising a response element that binds to a nuclear receptor of the Nur family of nuclear receptors, said response element comprising nucleotide sequence $X_8 L_6 Y_8$, wherein:
   a) $X_8$ and $Y_8$ are two half site sequences of 8 nucleotides which are configured as an everted repeat;
   b) $L_6$ separates said half site sequences, with L being 6 nucleotides and being independently selected from A,T,C,or G;
   c) $X_8$ having nucleotide sequence $N_6TT$, and $Y_8$ having nucleotide sequence $AAN_6$, wherein N is selected from A,T,C,or G, such that said sequence of $X_8$ and $Y_8$ share homology with the NBRE sequence defined by nucleotide the hexanucleotide sequence AGGTCA (SEQ ID NO: 3), and its complement TGACCT (SEQ ID NO: 29), respectively, and wherein said response element is capable of binding to a dimer consisting of two partners which are selected from members of the Nur family of nuclear receptors, comprising contacting a sample with said host cell according to claim 16, and comparing the level of expression of said reporter gene in the presence of the sample and in the absence thereof.

20. A method for measuring the ability of a compound to modulate transcription at a Nur response element (Nur-RE), wherein said Nur-RE is an oligonucleotide sequence comprising a response element that binds to a nuclear receptor of the Nur family of nuclear receptors, said response element comprising nucleotide sequence $X_8 L_6 Y_8$, wherein:
   a) $X_8$ and $Y_8$ are two half site sequences of 8 nucleotides which are configured as an everted repeat;

b) $L_6$ separates said half site sequences, with L being 6 nucleotides and being independently selected from A,T,C,or G;

c) $X_8$ having nucleotide sequence $N_6TT$, and $Y_8$ having nucleotide sequence $AAN_6$, wherein N is selected from A,T,C,or G such that said sequence of $X_8$ and $Y_8$ share homology with the NBRE sequence defined by nucleotide the hexanucleotide sequence AGGTCA (SEQ ID NO:3), and its complement TGACCT (SEQ ID NO: 29), respectively, and wherein said response element is capable of binding to a dimer consisting of two partners which are selected from members of the Nur family of nuclear receptors, comprising:

a) contacting said compound with said host cell of claim 16, under conditions conducive to the expression of said heterologous gene in response to said compound; and b) comparing the level of gene expression in step a) with the level of gene expression from said host cell in the absence of said compound.

21. The method of claim 20, whereby a ligand which is selective for Nur family transcriptional complexes is identified.

* * * * *

SEQUENCE LISTING

```
<160> NUMBER OF SEQ ID NOS: 33

<210> SEQ ID NO 1
<211> LENGTH: 8
<212> TYPE: DNA
<213> ORGANISM: Murinae gen. sp.

<400> SEQUENCE: 1 aaaggtca                                                             8

<210> SEQ ID NO 2
<211> LENGTH: 24
<212> TYPE: DNA
<213> ORGANISM: Murinae gen. sp.

<400> SEQUENCE: 2
gtgatattta cctccaaatg ccag                                          24

<210> SEQ ID NO 3
<211> LENGTH: 6
<212> TYPE: DNA
<213> ORGANISM: Murinae gen. sp.

<400> SEQUENCE: 3 aggtca                                                               6

<210> SEQ ID NO 4
<211> LENGTH: 28
<212> TYPE: DNA
<213> ORGANISM: Murinae gen. sp.

<400> SEQUENCE: 4
gatcctcgtg cgaaaaggtc aagcgcta                                      28

<210> SEQ ID NO 5
<211> LENGTH: 33
<212> TYPE: DNA
<213> ORGANISM: Murinae gen. sp.

<400> SEQUENCE: 5
gatcctagtg atatttacct ccaaatgcca gga                                33
```

-continued

<210> SEQ ID NO 6
<211> LENGTH: 22
<212> TYPE: DNA
<213> ORGANISM: Murinae gen. sp.

<400> SEQUENCE: 6
tgacctttat tctcaaaggt ca                                              22

<210> SEQ ID NO 7
<211> LENGTH: 8
<212> TYPE: DNA
<213> ORGANISM: Murinae gen. sp.

<400> SEQUENCE: 7 aaatatca                                                               8

<210> SEQ ID NO 8
<211> LENGTH: 8
<212> TYPE: DNA
<213> ORGANISM: Murinae gen. sp.

<400> SEQUENCE: 8 aaatgcca                                                               8

<210> SEQ ID NO 9
<211> LENGTH: 24
<212> TYPE: DNA
<213> ORGANISM: Murinae gen. sp.
<220> FEATURE:
<221> NAME/KEY: variation
<222> LOCATION: (10)..(15)
<223> OTHER INFORMATION: N = A, T, C or G

<400> SEQUENCE: 9
gtgatatttn nnnnaaatg ccag                                             24

<210> SEQ ID NO 10
<211> LENGTH: 22
<212> TYPE: DNA
<213> ORGANISM: Murinae gen. sp.
<220> FEATURE:
<221> NAME/KEY: variation
<222> LOCATION: (9)..(14)
<223> OTHER INFORMATION: N = A, T, C or G

<400> SEQUENCE: 10
tgatatttnn nnnaaatgc ca                                               22

<210> SEQ ID NO 11
<211> LENGTH: 24
<212> TYPE: DNA
<213> ORGANISM: Murinae gen. sp.
<220> FEATURE:
<221> NAME/KEY: variation
<222> LOCATION: (10)..(15)
<223> OTHER INFORMATION: N = A, T, C or G

<400> SEQUENCE: 11
gtgatatttn nnnnaaata tcac                                             24

<210> SEQ ID NO 12
<211> LENGTH: 22
<212> TYPE: DNA
<213> ORGANISM: Murinae gen. sp.
<220> FEATURE:
<221> NAME/KEY: variation

```
<222> LOCATION: (9)..(14)
<223> OTHER INFORMATION: N = A, T, C or G

<400> SEQUENCE: 12
tgatatttnn nnnnaaatat ca                                              22

<210> SEQ ID NO 13
<211> LENGTH: 24
<212> TYPE: DNA
<213> ORGANISM: Murinae gen. sp.
<220> FEATURE:
<221> NAME/KEY: variation
<222> LOCATION: (10)..(15)
<223> OTHER INFORMATION: N = A, T, C or G

<400> SEQUENCE: 13
ctggcatttn nnnnaaatg ccag                                             24

<210> SEQ ID NO 14
<211> LENGTH: 22
<212> TYPE: DNA
<213> ORGANISM: Murinae gen. sp.
<220> FEATURE:
<221> NAME/KEY: variation
<222> LOCATION: (9)..(14)
<223> OTHER INFORMATION: N = A, T, C or G

<400> SEQUENCE: 14
tggcatttnn nnnnaaatgc ca                                              22

<210> SEQ ID NO 15
<211> LENGTH: 24
<212> TYPE: DNA
<213> ORGANISM: Murinae gen. sp.
<220> FEATURE:
<221> NAME/KEY: variation
<222> LOCATION: (1)
<223> OTHER INFORMATION: N = C or G
<220> FEATURE:
<221> NAME/KEY: variation
<222> LOCATION: (10)..(15)
<223> OTHER INFORMATION: N = A, T, C or G
<220> FEATURE:
<221> NAME/KEY: variation
<222> LOCATION: (24)
<223> OTHER INFORMATION: N = C or G

<400> SEQUENCE: 15
ntgacctttn nnnnnaaagg tcan                                            24

<210> SEQ ID NO 16
<211> LENGTH: 22
<212> TYPE: DNA
<213> ORGANISM: Murinae gen. sp.
<220> FEATURE:
<221> NAME/KEY: variation
<222> LOCATION: (9)..(14)
<223> OTHER INFORMATION: N = A, T, C or G

<400> SEQUENCE: 16
tgacctttnn nnnnaaaggt ca                                              22

<210> SEQ ID NO 17
<211> LENGTH: 24
<212> TYPE: DNA
<213> ORGANISM: Murinae gen. sp.
<220> FEATURE:
<221> NAME/KEY: variation
<222> LOCATION: (1)
```

```
<223> OTHER INFORMATION: N = C or G
<220> FEATURE:
<221> NAME/KEY: variation
<222> LOCATION: (4)
<223> OTHER INFORMATION: N = A or G
<220> FEATURE:
<221> NAME/KEY: variation
<222> LOCATION: (10)..(15)
<223> OTHER INFORMATION: N = A, T, C or G
<220> FEATURE:
<221> NAME/KEY: variation
<222> LOCATION: (20)
<223> OTHER INFORMATION: N = A or G
<220> FEATURE:
<221> NAME/KEY: variation
<222> LOCATION: (24)
<223> OTHER INFORMATION: N = C or G

<400> SEQUENCE: 17
ntgnyatttn nnnnnaaatn ycan                                              24

<210> SEQ ID NO 18
<211> LENGTH: 22
<212> TYPE: DNA
<213> ORGANISM: Murinae gen. sp.
<220> FEATURE:
<221> NAME/KEY: variation
<222> LOCATION: (3)
<223> OTHER INFORMATION: N = A or G
<220> FEATURE:
<221> NAME/KEY: variation
<222> LOCATION: (9)..(14)
<223> OTHER INFORMATION: N = A, T, C or G
<220> FEATURE:
<221> NAME/KEY: variation
<222> LOCATION: (19)
<223> OTHER INFORMATION: N = A or G

<400> SEQUENCE: 18
tgnyatttnn nnnnaaatny ca                                                22

<210> SEQ ID NO 19
<211> LENGTH: 24
<212> TYPE: DNA
<213> ORGANISM: Murinae gen. sp.

<400> SEQUENCE: 19
gtgatattta cctccaaatg ccag                                              24

<210> SEQ ID NO 20
<211> LENGTH: 22
<212> TYPE: DNA
<213> ORGANISM: Murinae gen. sp.

<400> SEQUENCE: 20
tgatatttac ctccaaatgc ca                                                22

<210> SEQ ID NO 21
<211> LENGTH: 24
<212> TYPE: DNA
<213> ORGANISM: Murinae gen. sp.

<400> SEQUENCE: 21
gtgatattta cctccaaata tcac                                              24

<210> SEQ ID NO 22
<211> LENGTH: 22
<212> TYPE: DNA
<213> ORGANISM: Murinae gen. sp.
```

```
<400> SEQUENCE: 22
tgatatttac ctccaaatat ca                                        22

<210> SEQ ID NO 23
<211> LENGTH: 24
<212> TYPE: DNA
<213> ORGANISM: Murinae gen. sp.

<400> SEQUENCE: 23
ctggcattta cctccaaatg ccag                                      24

<210> SEQ ID NO 24
<211> LENGTH: 22
<212> TYPE: DNA
<213> ORGANISM: Murinae gen. sp.

<400> SEQUENCE: 24
tggcatttac ctccaaatgc ca                                        22

<210> SEQ ID NO 25
<211> LENGTH: 24
<212> TYPE: DNA
<213> ORGANISM: Murinae gen. sp.
<220> FEATURE:
<221> NAME/KEY: variation
<222> LOCATION: (1)
<223> OTHER INFORMATION: N =  C or G
<220> FEATURE:
<221> NAME/KEY: variation
<222> LOCATION: (24)
<223> OTHER INFORMATION: N =  C or G

<400> SEQUENCE: 25 ntgacctttta cctccaaagg tcan                                     24

<210> SEQ ID NO 26
<211> LENGTH: 22
<212> TYPE: DNA
<213> ORGANISM: Murinae gen. sp.

<400> SEQUENCE: 26
tgacctttac ctccaaaggt ca                                        22

<210> SEQ ID NO 27
<211> LENGTH: 24
<212> TYPE: DNA
<213> ORGANISM: Murinae gen. sp.
<220> FEATURE:
<221> NAME/KEY: variation
<222> LOCATION: (1)
<223> OTHER INFORMATION: N =  C or G
<220> FEATURE:
<221> NAME/KEY: variation
<222> LOCATION: (4)
<223> OTHER INFORMATION: N = A or G
<220> FEATURE:
<221> NAME/KEY: variation
<222> LOCATION: (20)
<223> OTHER INFORMATION: N = A or G
<220> FEATURE:
<221> NAME/KEY: variation
<222> LOCATION: (24)
<223> OTHER INFORMATION: N = C or G

<400> SEQUENCE: 27
ntgnyattta cctccaaatn ycan                                      24
```

```
<210> SEQ ID NO 28
<211> LENGTH: 22
<212> TYPE: DNA
<213> ORGANISM: Murinae gen. sp.
<220> FEATURE:
<221> NAME/KEY: variation
<222> LOCATION: (3)
<223> OTHER INFORMATION: N = A or G
<220> FEATURE:
<221> NAME/KEY: variation
<222> LOCATION: (19)
<223> OTHER INFORMATION: N = A or G

<400> SEQUENCE: 28
tgnyatttac ctccaaatny ca                                              22

<210> SEQ ID NO 29
<211> LENGTH: 6
<212> TYPE: DNA
<213> ORGANISM: Murinae gen. sp.

<400> SEQUENCE: 29 tgacct                                                                 6

<210> SEQ ID NO 30
<211> LENGTH: 8
<212> TYPE: DNA
<213> ORGANISM: Murinae gen. sp.

<400> SEQUENCE: 30 tgatattt                                                               8

<210> SEQ ID NO 31
<211> LENGTH: 8
<212> TYPE: DNA
<213> ORGANISM: Murinae gen. sp.

<400> SEQUENCE: 31 tggcattt                                                               8

<210> SEQ ID NO 32
<211> LENGTH: 8
<212> TYPE: DNA
<213> ORGANISM: Murinae gen. sp.

<400> SEQUENCE: 32 tgaccttt                                                               8

<210> SEQ ID NO 33
<211> LENGTH: 22
<212> TYPE: DNA
<213> ORGANISM: Murinae gen. sp.

<400> SEQUENCE: 33
tgacctttat tctcaaaggt ca                                              22
```